US011213543B2

(12) United States Patent
Heiman et al.

(10) Patent No.: US 11,213,543 B2
(45) Date of Patent: *Jan. 4, 2022

(54) HUMAN GASTROINTESTINAL MICROBIOME MODULATING COMPOSITION AND METHODS OF USE

(71) Applicant: The Nature's Bounty Co., Ronkonkoma, NY (US)

(72) Inventors: Mark L. Heiman, Indianapolis, IN (US); Dean P. Stull, Longmont, CO (US); Justin W. Peno, Saint Francisville, LA (US)

(73) Assignee: THE NATURE'S BOUNTY CO., Ronkonkoma, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/545,249

(22) Filed: Aug. 20, 2019

(65) Prior Publication Data

US 2019/0374570 A1 Dec. 12, 2019

Related U.S. Application Data

(62) Division of application No. 15/288,533, filed on Oct. 7, 2016, now Pat. No. 10,441,602, which is a division of application No. 14/238,980, filed as application No. PCT/US2012/051408 on Aug. 17, 2012, now Pat. No. 9,463,169.

(60) Provisional application No. 61/524,524, filed on Aug. 17, 2011.

(51) Int. Cl.
| | |
|---|---|
| *A61K 36/00* | (2006.01) |
| *A61K 31/733* | (2006.01) |
| *A23L 29/212* | (2016.01) |
| *A23L 33/00* | (2016.01) |
| *A23L 33/105* | (2016.01) |
| *A23L 33/21* | (2016.01) |
| *A61K 31/047* | (2006.01) |
| *A61K 31/716* | (2006.01) |
| *A61K 31/718* | (2006.01) |
| *A61K 9/00* | (2006.01) |
| *A61K 36/45* | (2006.01) |
| *A61K 31/155* | (2006.01) |
| *A61K 38/28* | (2006.01) |
| *A61K 31/05* | (2006.01) |
| *A61K 36/88* | (2006.01) |
| *A61K 36/899* | (2006.01) |
| *A61K 9/10* | (2006.01) |

(52) U.S. Cl.
CPC ......... *A61K 31/733* (2013.01); *A23L 29/212* (2016.08); *A23L 33/00* (2016.08); *A23L 33/105* (2016.08); *A23L 33/21* (2016.08); *A23L 33/30* (2016.08); *A61K 9/0095* (2013.01); *A61K 31/047* (2013.01); *A61K 31/05* (2013.01); *A61K 31/155* (2013.01); *A61K 31/716* (2013.01); *A61K 31/718* (2013.01); *A61K 36/00* (2013.01); *A61K 36/45* (2013.01); *A61K 36/88* (2013.01); *A61K 36/899* (2013.01); *A61K 38/28* (2013.01); *A23V 2002/00* (2013.01); *A61K 9/0031* (2013.01); *A61K 9/10* (2013.01)

(58) Field of Classification Search
CPC ...................................................... A61K 36/00
USPC ...................................................... 424/725
See application file for complete search history.

(56) References Cited

U.S. PATENT DOCUMENTS

| | | | |
|---|---|---|---|
| 6,277,434 | B1 | 8/2001 | Matluk-Boisseau |
| 9,040,101 | B2 | 5/2015 | Heiman et al. |
| 9,463,169 | B2 | 10/2016 | Heiman et al. |
| 2002/0009436 | A1 | 1/2002 | Doyle et al. |
| 2004/0132164 | A1 | 7/2004 | Doyle et al. |
| 2005/0239706 | A1 | 10/2005 | Backhed et al. |
| 2007/0036836 | A1 | 2/2007 | Faure et al. |
| 2007/0196890 | A1 | 8/2007 | Vulevic et al. |
| 2008/0102162 | A1 | 5/2008 | Delcour et al. |
| 2008/0261916 | A1 | 10/2008 | Jaszberenyl et al. |
| 2008/0274127 | A1 | 11/2008 | Faure et al. |
| 2009/0142442 | A1 | 6/2009 | Rochat et al. |
| 2009/0148414 | A1 | 6/2009 | O'Doherty et al. |
| 2009/0170141 | A1 | 7/2009 | Brown et al. |
| 2009/0311370 | A1 | 12/2009 | Ogura et al. |
| 2010/0040745 | A1 | 2/2010 | Capodieci |
| 2010/0048595 | A1 | 2/2010 | Gordon et al. |
| 2010/0086527 | A1 | 4/2010 | Huber-Haag et al. |
| 2010/0086955 | A1 | 4/2010 | Harran et al. |

(Continued)

FOREIGN PATENT DOCUMENTS

| | | |
|---|---|---|
| EP | 1214893 A1 | 6/2002 |
| EP | 1600061 A1 | 11/2005 |

(Continued)

OTHER PUBLICATIONS

Extended European Search Report, Application No. EP12827673, dated Aug. 31, 2015.

(Continued)

*Primary Examiner* — Michael V Meller
(74) *Attorney, Agent, or Firm* — Hoffman and Baron, LLP

(57) ABSTRACT

A formulation to increase the ratio of gastrointestinal microbiota in phylum Bacteroidetes to microbiota of Firmicutes phylum preferably includes about 20-60 mg/kg of body weight of fermentable fiber, about 10-30 mg/kg of body weight of beta glucan and about 20-60 mg/kg of body weight of blueberry extracts or any fruit or berry ingredient preparation containing similar phenolics. This formulation is preferably used to control body weight, body composition, and blood glucose regulation, preferably in humans, and is preferably administered orally, preferably twice per day.

22 Claims, 2 Drawing Sheets

(56) References Cited

U.S. PATENT DOCUMENTS

| | | |
|---|---|---|
| 2010/0129818 A1 | 5/2010 | Sadee et al. |
| 2010/0172874 A1 | 7/2010 | Turnbaugh et al. |
| 2010/0254949 A1 | 10/2010 | Barboza et al. |
| 2010/0317573 A1 | 12/2010 | Goedhart et al. |
| 2011/0009359 A1 | 1/2011 | Amor et al. |
| 2011/0034407 A1 | 2/2011 | Nieuwenhuizen et al. |
| 2011/0123501 A1 | 5/2011 | Chou et al. |
| 2011/0280840 A1 | 11/2011 | Blaser et al. |
| 2012/0027724 A1 | 2/2012 | Brinkmann et al. |
| 2012/0058094 A1 | 3/2012 | Blaser et al. |
| 2012/0135957 A1 | 5/2012 | Dugenet et al. |
| 2014/0294997 A1 | 10/2014 | Heiman et al. |
| 2015/0118330 A1 | 4/2015 | Heiman et al. |

FOREIGN PATENT DOCUMENTS

| | | |
|---|---|---|
| EP | 2102350 A2 | 9/2009 |
| JP | 2001046030 A | 2/2001 |
| JP | 2009263655 A | 11/2009 |
| JP | 2014528925 A | 10/2014 |
| JP | 5877902 B2 | 3/2016 |
| WO | 2000064282 A1 | 11/2000 |
| WO | 2007142306 A1 | 12/2007 |
| WO | 2008076696 A2 | 6/2008 |
| WO | 2010002890 A2 | 1/2010 |
| WO | 2010151842 A2 | 12/2010 |
| WO | 2011022660 A1 | 2/2011 |
| WO | 2011060307 A2 | 5/2011 |
| WO | 2011103123 A2 | 8/2011 |
| WO | 2011107482 A2 | 9/2011 |
| WO | 2012024638 A2 | 2/2012 |
| WO | 2013032744 A2 | 3/2013 |

OTHER PUBLICATIONS

Office Action, Japanese Patent Application No. 2014-526252, dated May 11, 2015.
Stull, A.J., et al., "Bioactives in Blueberries Improve Insulin Sensitivity in Obese, Insulin-Resistant Men and Women", J. Nutr., 104:1764-1768 (2010).
American Diabetes Association,"Standards of Medical Care in Diabetes—2012," Diabetes care 35.Supplement 1 S11-S63 (2012).
Borody, Thomas J., et al., "Fecal Microbiota Transplantation and Emerging Applications," Nature Reviews Gastroenterology & Hepatology, 9.2:88-96 (2012).
Cavet, Megan E., et al. "Anti-Inflammatory and Anti-Oxidative Effects of the Green Tea Polyphenol Epigallocatechin gallate in Human Corneal Epithelial Cells," Molecular Vision,17: 533 (2011).
Dandona, Paresh, et al. "Diarrhea and Metformin in a Diabetic Clinic," Diabetes care 6.5 : 472-474 (1983).
De Filippo, Carlotta, et al. "Impact of Diet in Shaping Gut Microbiota Revealed by a Comparative Study in Children from Europe and Rural Africa," Proceedings of the National Academy of Sciences, 107.33 : 14691-14696 (2010).
De Vriese, Carine, et al. "Ghrelin Degradation by Serum and Tissue Homogenates: Identification of the Cleavage Sites," Endocrinology, 145.11 : 4997-5005 (2004).
Gauna, Carlotta, et al. "Unacylated Ghrelin Acts as a Potent Insulin Secretagogue in Glucose-Stimulated Conditions," American Journal of Physiology-Endocrinology and Metabolism, 293.3 : E697-E704 (2007).
Gibson, Glenn R., et al. "Dietary Modulation of the Human Colonic Microbiota: Updating the Concept of Prebiotics," Nutrition Research Reviews, 17.2 : 259-275 (2004).
Goodman, Andrew L., et al. "Extensive Personal Human Gut Microbiota Culture Collections Characterized and Manipulated in Gnotobiotic Mice," Proceedings of the National Academy of Sciences, 108.15 : 6252-6257 (2011).
Gutierrez, Jesus A., et al. "Ghrelin Octanoylation Mediated by an Orphan Lipid Transferase," Proceedings of the National Academy of Sciences, 105.17 : 6320-6325 (2008).
Islam, Kbm Saiful, et al. "Bile Acid is a Host Factor that Regulates the Composition of the Cecal Microbiota in Rats," Gastroenterology, 141.5 : 1773-1781 (2011).
Juhel, Christine, et al. "Cholesterol-Lowering Effect of Non-Viscous Soluble Dietary Fiber Nutriose (R) 6 in Moderately Hypercholesterolemic Hamsters," Indian Journal of Experimental Biology, 49.3 : 219-228 (2011).
Kahle, Kathrin, et al. "Studies on Apple and Blueberry Fruit Constituents: Do the Polyphenols Reach the Colon After Ingestion?," Molecular Nutrition & Food Research, 50.4-5 : 418-423 (2006).
Kalra, Sanjay, "Emerging Role of Dipeptidyl Peptidase-IV (DPP-4) Inhibitor Vildagliptin in the Management of Type 2 Diabetes," J Assoc Physicians India, 59.2 : 237-245 (2011).
Kirchner, Henriette, et al. "GOAT Links Dietary Lipids with the Endocrine Control of Energy Balance," Nature Medicine, 15.7 : 741-745 (2009).
Kojima, Masayasu, et al. "Ghrelin is a Growth-Hormone-Releasing Acylated Peptide from Stomach," Nature 402.6762 : 656-660 (1999).
Ley, Ruth E., et al. "Obesity Alters Gut Microbial Ecology," Proceedings of the National Aacademy of Sciences 102.31 : 11070-11075 (2005).
Li, Yue, et al. "Protective Effect of Dietary Fiber on Intestinal Mucosa Barrier in Inflammatory Bowel Diseases Rats," China Medical Herald, 13 : 22-23 (2010).
Lia, Agot, et al. "Oat Beta-Glucan Increases Bile Acid Excretion and a Fiber-Rich Barley Fraction Increases Cholesterol Excretion in Ileostomy Subjects," The American Journal of Clinical Nutrition, 62.6 : 1245-1251 (1995).
Manach, Claudine, et al. "Polyphenols: Food Sources and Bioavailability," The American Journal of Clinical Nutrition, 79.5 : 727-747 (2004).
Matsumoto, Masaru, et al. "Structure-Activity Relationship of Ghrelin: Pharmacological Study of Ghrelin Peptides," Biochemical and Biophysical Research Communications, 287.1 : 142-146 (2001).
Orešič, Matej, et al. "Gut Microbiota Affects Lens and Retinal Lipid Composition," Experimental Eye Research, 89.5 : 604-607 (2009).
Puupponen-Pimiä, Riitta, et al. "Antimicrobial Properties of Phenolic Compounds from Berries," Journal of Applied Microbiology, 90.4 : 494-507 (2001).
Puupponen-Pimiä, Riitta, et al. "Berry Phenolics Selectively Inhibit the Growth ofl Intestinal Pathogens," Journal of Applied Microbiology, 98.4 : 991-1000 (2005).
Rajilić-Stojanović, Mirjana, et al. "Global and Deep Molecular Analysis of Microbiota Signatures in Fecal Samples from Patients with Irritable Bowel Syndrome," Gastroenterology, 141.5 :1792-1801 (2011).
Rolando, Maurizio, et al., "The Ocular Surface and Tear Film and Their Dysfunction in Dry Eye Disease," Survey of Ophthalmology, 45 : S203-S210 (2001).
Sonnenburg, Justin L., et al. "Glycan Foraging in Vivo by an Intestine-Adapted Bacterial Symbiont," Science, 307.5717 : 1955-1959(2005). DOI: 10.1126/science.1109051.
Tarini, Joshua, et al., "The Fermentable Fibre Inulin Increases Postprandial Serum Short-Chain Fatty Acids and Reduces Free-Fatty Acids and Ghrelin in Healthy Subjects," Applied Physiology, Nutrition, and Metabolism, 35.1 : 9-16 (2010).
Turnbaugh, Peter J., et al. "An Obesity-Associated Gut Microbiome with Increased Capacity for Energy Harvest," Nature, 444.7122 : 1027 (2006).
Turnbaugh, Peter J., et al. "A Core Gut Microbiome in Obese and Lean Twins," Nature, 457.7228 : 480-484 (2009).
Turnbaugh, Peter J., et al. "The Effect of Diet on the Human Gut Microbiome: A Metagenomic Analysis in Humanized Gnotobiotic Mice," Science Translational Medicine, 1.6 : 6ra14-6ra14 (2009).
Van Kooyk, Yvette, et al.,. "Protein-Glycan Interactions in the Control of Innate and Adaptive Immune Responses," Nature Immunology, 9.6 : 593-601 (2008).
Vos Ap, et al., "Immune-Modulatory Effects and Potential Working Mechanisms of Orally Applied Nondigestible Carbohydrates," Crit Rev Immunol., 27(2):97-140 2007. doi: 10.1615/critrevimmunol. v27.i2.10. PMID: 17725499.

(56) References Cited

OTHER PUBLICATIONS

Vrieze, Anne, et al. "Transfer of Intestinal Microbiota from Lean Donors Increases Insulin Sensitivity in Individuals with Metabolic Syndrome," Gastroenterology, 143.4 : 913-916 (2012).
Yang, Jing, et al. "Identification of the Acyltransferase that Octanoylates Ghrelin, an Appetite-Stimulating Peptide Hormone," Cell 132.3 : 387-396 (2008).
International Search Report in PCT/US2012/051408, dated Apr. 18, 2013.
Written Opinion in PCT/US2012/051408, dated Apr. 18, 2013.
International Preliminary Report on Patentability in PCT/US2012/051408 dated Feb. 18, 2014.
Greenway, F., "A Novel Cobiotic Containing a Prebiotic and an Antioxidant Augments the Glucose Control and Gastrointestinal Tolerability of Metformin: A Case Report," Beneficial Microbes, 5.1 : 29-32 (2014).
Burton, Jeffrey H., et al. "Addition of a Gastrointestinal Microbiome Modulator to Metformin Improves Metformin Tolerance and Fasting Glucose Levels," Journal of Diabetes Science and Technology, 9.4 : 808-814 (2015).
Rebello, Candida J., et al. "Gastrointestinal Microbiome Modulator Improves Glucose Tolerance in Overweight and Obese Subjects: A Randomized Controlled Pilot Trial," Journal of Diabetes and its Complications, 29.8 : 1272-1276 (2015).
Koruri, S. Samanta, et al. "Studies on Prebiotic Food Additive (Inulin) in Indian Dietary Fibre Sources-Garlic (*Allium sativum*), Wheat (*Triticum* spp ), Aat (*Avena sativa*) and Dalia (*Bulgur*)," International Journal of Pharmacy and Pharmaceutical Sciences, 6.9 278-282 (2014).
Office Action (English translation), Japanese Patent Application No. 2016-012347, dated Oct. 25, 2016.
WebMD, "Beta Glucans Overview Information, Uses, Side Effects, Interactions, and Warnings", 2009.

HUMAN GASTROINTESTINAL MICROBIOME MODULATING COMPOSITION AND METHODS OF USE

CROSS REFERENCE TO RELATED APPLICATIONS

The present application is a Divisional Application, which claims priority to U.S. application Ser. No. 15/288,533, filed on Oct. 7, 2016, which claims priority to U.S. application Ser. No. 14/238,980, filed on Jun. 5, 2014, which is a U.S. National Stage Application pursuant to 35 U.S.C. § 371 of International Application No. PCT/US2012/051408, filed on Aug. 17, 2012, which claims priority to U.S. Provisional Application No. 61/524,524, filed on Aug. 17, 2011, each of which are hereby incorporated by reference in their entireties.

BACKGROUND OF THE INVENTION

1. Field of the Invention

The present invention relates to weigh control and metabolic fitness. More particularly, the present invention relates to compositions and methods for increasing desirable microbiota in the human gut and reducing therein undesirable microbiota to achieve a healthy glucose regulation, metabolic fitness, inclusive intestinal health, and a healthy body weight.

2. General Background of the Invention

During the past 5 years a large international effort, called the Human Microbiome Project (HMP) by the National Institutes of Health, and known more broadly as the International Human Microbiome Consortium (IHMC), is aimed at characterizing the microbes living in and on our bodies (see http://hmpdacc.org/data_browser.php). In the large intestine an estimated 100 trillion microorganisms reside that appear to play essential roles in metabolizing food, drugs, and dietary supplements that are not absorbed by the upper gastrointestinal (GI) tract. In addition, some of those microorganisms manufacture essential nutrients and vitamins necessary to sustain health. Such microbial interactions in the intestinal environment exert critical roles in signaling metabolic-, behavior-, and immune-regulatory systems of the human host.

The first GI microbiomes to be partially characterized are those obtained in the feces of obese and lean individuals (1,2). Microbiota of the Firmicutes phylum are in abundance in the feces of obese individuals when compared to that of lean volunteers. Microbiota of the other major division, Bacteroidetes, are more abundant than those of Firmicutes division in lean individuals. Thus, during metabolic diseases such as obesity and diabetes, an imbalance between these 2 dominant groups of bacteria reflecting a wealth of Firmuctes species to Bacteroidetes species (B:F ratio) is one characteristic of individuals with an unhealthy body mass. These findings are confirmed in obese and lean mice (3). Further, sterile mice can be inoculated with microbiomes obtained from human feces of either obese or lean individuals. When fed a standard mouse chow, they either become obese or remain lean depending on the source of their GI microbiota transplant (4). Mice transplanted with human GI microbiota will become obese when fed a chow rich in simple sugars and fat after several weeks. The B:F ratio of those mice is increased when the diet is switched to one low in both fat and sugar but rich in plant polysaccharides (5,6).

Microbiota belonging to the Bacteriodetes phylum are specialists at transporting and metabolizing carbohydrates (7). They appear to forage on any available carbohydrate in their environment. Most sugars and starches, however, are metabolized by the host and are absorbed by the upper GI. Indigestible (by the host) carbohydrates do make it to the lower GI where they are consumed by members of the Bacteriodetes. The end products of this process are small chain fatty acids (SCFAs) that have health benefits for the host. Many of these indigestible carbohydrates are plant polysaccharides or more commonly called fiber or resistant starch and are classified as prebiotics (8). Microbiomes characterized in the feces of children maintained on a high fiber diet have a greater B:F ratio than those analyzed from feces of children consuming a typical European diet (9).

The following U.S. and other patent documents are incorporated herein by reference:
US20020009436 Methods and compositions for inhibiting adhesion by microorganisms
US20040132164 Methods and compositions for inhibiting adhesion by microorganisms
US20050239706 Modulation of fiaf and the gastrointestinal microbiota as a means to control energy storage in a subject
US20070036836 Amino acid supplementation for a healthy microbiota ecosystem
US20070196890 Prebiotic effect analysis
US20080102162 Prebiotic Preparation
US20080261916 Synergistic Prebiotic Compositions
US20080274127 AMINO ACID SUPPLEMENTATION FOR A HEALTHY MICROBIOTA ECOSYSTEM
US20090142442 GUT MICROBIOTA IN INFANTS
US20090148414 Novel Composition to Improve Gut Health and Animal Performance and Methods of Making the Same
US20090170141 GHRELIN O-ACYLTRANSFERASE (GOAT) BIOCHEMICAL ASSAY
US20100048595 USE OF ARCHAEA TO MODULATE THE NUTRIENT HARVESTING FUNCTIONS OF THE GASTROINTESTINAL MICROBIOTA
US20100086527 SYNBIOTIC TO IMPROVE GUT MICROBIOTA
US20100086955 Small Molecule Inhibitors of Ghrelin O-Acyltransferase
US20100129816 Microbial Population Analysis
US20100172874 GUT MICROBIOME AS A BIOMARKER AND THERAPEUTIC TARGET FOR TREATING OBESITY OR AN OBESITY RELATED DISORDER
US20100254949 PREBIOTIC OLIGOSACCHARIDES
US20100317573 PEDIATRIC FIBER MIXTURE
US20110009359 USE OF NON-DIGESTIBLE CARBOHYDRATES FOR IMPROVING INTESTINAL MICROBIOTA
US20110034407 USE OF SPHINGOMYELIN AND NON-DIGESTIBLE CARBOHYDRATES FOR IMPROVING INTESTINAL MICROBIOTA
US20110123501 GUT FLORA AND WEIGHT MANAGEMENT
US20050239706 MODULATION OF FIAF AND THE GASTROINTESTINAL MICROBIOTA AS A MEANS TO CONTROL ENERGY STORAGE IN A SUBJECT
US20110280840 COMPOSITIONS AND METHODS FOR TREATING OBESITY AND RELATED DISOR-

DERS BY CHARACTERIZING AND RESTORING MAMMALIAN BACTERIAL MICROBIOTA

US20120027724 METHODS OF TREATING IMPAIRED GLUCOSE METABOLISM VIA ADMINISTRATION OF ALGAL BIOMASS

US20120058094 COMPOSITIONS AND METHODS FOR TREATING OBESITY AND RELATED DISORDERS BY CHARACTERIZING AND RESTORING MAMMALIAN BACTERIAL MICROBIOTA

US20120135957 COMPOSITIONS CONTAINING MIXTURES OF FERMENTABLE FIBERS

WO/2012/024638A2 COMPOSITIONS AND METHODS FOR TREATING OBESITY AND RELATED DISORDERS BY CHARACTERIZING AND RESTORING MAMMALIAN BACTERIAL MICROBIOTA

WO/2011/107482A9 METHOD OF DIAGNOSTIC OF OBESITY

WO/2011/103123A2 REDUCING SHORT-CHAIN FATTY ACIDS AND ENERGY UPTAKE IN OBESE HUMANS BY MANAGING THEIR INTESTINAL MICROBIAL COMMUNITIES

WO/2011/022660A1 METHODS OF DIAGNOSING AND TREATING MICROBIOME-ASSOCIATED DISEASE USING INTERACTION NETWORK PARAMETERS

WO/2008/076696A2 THE GUT MICROBIOME AS A BIOMARKER AND THERAPEUTIC TARGET FOR TREATING OBESITY OR AN OBESITY RELATED DISORDER

WO/2008/076696A3 THE GUT MICROBIOME AS A BIOMARKER AND THERAPEUTIC TARGET FOR TREATING OBESITY OR AN OBESITY RELATED DISORDER

WO/2010/002890A2 METHODS OF PROMOTING WEIGHT LOSS AND ASSOCIATED ARRAYS

WO/2010/002890A3 METHODS OF PROMOTING WEIGHT LOSS AND ASSOCIATED ARRAYS

WO/2010/151842A2 METHODS AND SYSTEMS FOR PHYLOGENETIC ANALYSIS

EP2102350A2 THE GUT MICROBIOME AS A BIOMARKER AND THERAPEUTIC TARGET FOR TREATING OBESITY OR AN OBESITY RELATED DISORDER

Also incorporated herein by reference are the following references, which are referenced above and below:

1. Peter J. Turnbaugh, Ruth E. Ley, Michael A. Mahowald, Vincent Magrini, Elaine R. Mardis, Jeffrey I. Gordon. An obesity-associated gut microbiome with increased capacity for energy harvest. Nature 444, 1027-1031, 2006.
2. Peter J. Turnbaugh, Micah Hamady, Tanya Yatsunenko, Brandi L. Cantarel, Alexis Duncan, Ruth E. Ley, Mitchell L. Sogin, William J. Jones, Bruce A. Roe, Jason P. Affourtit, et al. A core gut microbiome in obese and lean twins. Nature 457, 480-484, 2008.
3. Ruth E. Ley, Fredrik Biickhed, Peter Turnbaugh, Catherine A. Lozupone, Robin D. Knight, and Jeffrey 1. Gordon. Obesity alters gut microbial ecology. PNAS 102: 11070-11075, 2005.
4. Peter J. Tumbaugh, Ruth E. Ley, Michael A. Mahowald, Vincent Magrini, Elaine R. Mardis & Jeffrey I. Gordon. An obesity-associated gut microbiome with increased capacity for energy harvest. Nature 444: 1027-1031, 2006.
5. Andrew L. Goodman, George Kallstrom, Jeremiah J. Faith, Alejandro Reyes, Aimee Moore, Gautam Dantas, and Jeffrey I. Gordon. Extensive personal human gut microbiota culture collections characterized and manipulated in gnotobiotic mice. PNAS 108: 6252-6257, 2011
6. Peter J. Turnbaugh, Vanessa K. Ridaura, Jeremiah J. Faith, Federico E. Rey, Rob Knight, and Jeffrey I. Gordon. The Effect of Diet on the Human Gut Microbiome: A Metagenomic Analysis in Humanized Gnotobiotic Mice. Sci Transl Med 1: 1-10, 2009.
7. Justin L. Sonnenburg, Jian Xu. Douglas D. Leip, Chien-Huan Chen, Benjamin P. Westover, Jeremy Weatherford, Jeremy D. Buhler, and Jeffrey 1. Gordon. Glycan Foraging in Vivo by an Intestine-Adapted Bacterial Symbiont. Science 307: 1955-1959, 2005.
8. Glenn R. Gibson, Hollie M. Probert, Jan Van Loo, Robert A. Rastall and Marcel B. Roberfroid. Dietary modulation of the human colonic microbiota: updating the concept of prebiotics. Nutr. Res. Rev. 17: 259-275, 2004.
9. Carlotta De Filippo, Duccio Cavalieri, Monica Di Paola, Matteo Ramazzotti, Jean Baptiste Poullet, Sebastien Massart, Silvia Collini, Giuseppe Pieraccini, and Paolo Lionetti. Impact of diet in shaping gut microbiota revealed by a comparative study in children from Europe and rural Africa. PNAS 107: 14691-14696, 2010.
10. Kojima M, Hosoda H, Date Y, Nakazato M, Matsuo H, Kangawa K. 1999 Ghrelin is a growth-hormone-releasing acylated peptide from stomach. Nature 402: 656-60.
11. Carine De Vriese, Francoise Gregoire, Roger Lema-Kisoka, Magali Waelbroeck, Patrick Robberecht and Christine Delporte. Ghrelin Degradation by Serum and Tissue Homogenates: Identification of the Cleavage Sites. Endocrinol 145: 1 4997-5005, 2005.
12. Carlotta Gauna, Rosalie M. Kiewiet, Joop A. M. J. L. Janssen, Bedette van de Zande, Patric J. D. Delhanty, Ezio Ghigo, Leo J. Hofland, Axel P. N. Themmen, and Aart Jan van der Lely. Unacylated ghrelin acts as a potent insulin secretagogue in glucose-stimulated conditions *Am J Physiol Endocrinol Metab* 293: E697-E704, 2007.
13. Gutierrez, J. A. et al. Ghrelin octanoylation mediated by an orphan lipid transferase. *Proc Natl Acad Sci USA* 105, 6320-5 (2008).
14. Yang, J., Brown, M. S., Liang, G., Grishin, N. V. & Goldstein, J. L. Identification of the acyltransferase that octanoylates ghrelin, an appetite-stimulating peptide hormone. *Cell* 132, 387-96 (2008).
15. Matsumoto M, Hosoda H, Kitajima Y, Morozumi N, Minamitake Y, Tanaka S, Matsuo H, Kojima M, Hayashi Y, Kangawa K. Structure-activity relationship of ghrelin: pharmacological study of ghrelin peptides. Biochem Biophys Res Commun. 2001 Sep. 14; 287(1):142-6.
16. Kirchner, H., Gutierrez, J. A., Solenberg, P J., Pfluger, P. T., Czyzyk, T. A., Willency, J. A., Schurmann, A., Joost, H. G., Jandacek, R J., Hale, J. E., et al. (2009). Nat. Med. 15, 741-745.
17. Yvette van Kooyk and Gabriel A Rabinovich. Protein-glycan interactions in the control of innate and adaptive immune responses. Nat Immunol 9: 593-601, 2008.
18. Claudine Manach, Augustin Scalbert, Christine Morand, Christian Rémésy, and Liliana Jiménez. Polyphenols: food sources and bioavailability. Am J Clin Nutr 79:727-47, 2004.
19. Kathrin Kahle, Michael Kraus, Wolfgang Scheppach, Matthias Ackermann,
Friederike Ridder, and Elke Richling. Studies on apple and blueberry fruit constituents: do the polyphenols reach the colon after ingestion? Mol. Nutr. Food Res. 50: 418-423, 2006.
20. R. Puupponen-Pimiä, L. Nohynek, C. Meier, M. Kähkönen, M. Heinonen, A. Hopia, and K.-M. Oksman- Caldentey. Antimicrobial properties of phenolic compounds from berries. J Appl Microbiol 90: 494-507, 2001.
21. R. Puupponen-Pimiä, L. Nohynek, S. Hartmann-Schmidlin, M. Kähkönen, M. Heinonen, K. Määttä-Riihinen and K.-M. Oksman-Caldentey. Berry phenolics selectively inhibit the growth of intestinal pathogens. J Appl Microbiol 98: 991-1000, 2005.
22. U. S. Department of Agriculture, Agricultural Research Service. 2010. USDA National Nutrient Database for Standard Reference, Release 23. Nutrient Data Laboratory Home Page, http://www.ars.usda.gov/nutrientdata
23. A. J. Stull, K. C. Cash, W. D. Johnson, C. M. Champagne, and W. T. Cefalu. Bioactives in Blueberries Improve Insulin Sensitivity in Obese, Insulin-Resistant Men and Women. J. Nutr. 140: 1764-1768, 2010.
24. K. B. M. S Islam, S. Fukiya, M. Hagio, N. Fujii, S. Ishizuka, T. Ooka, Y. Ogura, T.
Hayashi, A.Yokota. Bile Acid is a Host Factor that Regulates the Composition of the Cecal Microbiota in Rats, Gastroenterology (2011),
doi:10.1053/j.gastro.2011.07.046.25. L. Agot Lia, G. Hallmans, A. Sandberg, B. Sundberg, P. Aman, and H. Andersson. Oat Beta glucan increases bile acid excretion and a fiber-rich barley fraction increases cholesterol excretion in ileostomy subjects. Am J Clin Nutr 1995; 62:1245-51.
26. American Diabetes Association. Diabetes Care. 2012; 35(suppl. 1):S1 1-S63.
27. Nandona P, Fonseca V, Mier A, Beckett A. Diarrhea and metformin in a diabetic clinic. Diabetes Care. 1983:6: 472-4.
28. M. Rajilić-Stojanović, E. Biagii, H. G. H. J. Heilig, K. Kajander, R. A. Kekkonen, S. Tims, and W. M. de Vos. Global and Deep Molecular Analysis of Microbiota Signatures in Fecal Samples from Patients with Irritable Bowel Syndrome. Gastroenterology 2011 November; 141 (5):1792-801.
29. T. J. Borody and A. Khoruts. Fecal microbiota transplantation and emerging applications. Nature Reviews Gastroenterology and Hepatology 9, 88-96, 2012.
30. A. Vrieze, E. van Nood, F. Holleman, J. Salojärvi, R. S. Kootte, J. F. W. M. Bartelsman, G. M. Dallinga-Thie, M. T. Ackermans, M. J. Serlie, R. Oozeer, M. Derrien, A. Druesne, J. E. T. van Hylckama Vlieg, V. W. Bloks, A. K. Groen, H. G. H. J. Heilig, E. G. Zoetendal, E. S. Stroes, W. M. de Vos, J. B. L. Hoekstra, M. Nieuwdorp. Transfer of Intestinal Microbiota from Lean Donors Increases Insulin Sensitivity in Subjects with Metabolic Syndrome. *Gastroenterology* (2012), doi: 10.1053/j.gastro.2012.06.031.
31. M. Orešič, T. Seppanen-Laakso, L. Yetukuri, F. Bäckhed, and V. Hänninen. Gut microbiota affects lens and retinal lipid composition. Experimental Eye Research 89 (2009) 604-607.
32. M. Rolando and M. Zierhut. The Ocular Surface and TearFilm and Their Dysfunction in Dry Eye Disease. Survey of Opthalamology 45, Suppl 2, S203-S210, 2001.

BRIEF SUMMARY OF THE INVENTION

The present invention includes a composition and use of a formulation to increase the ratio of gastrointestinal microbiota in phylum Bacteroidetes to microbiota of Firmicutes phylum.

BRIEF DESCRIPTION OF THE DRAWINGS

For a further understanding of the nature, objects, and advantages of the present invention, reference should be had to the following detailed description, read in conjunction with the following drawings, wherein.

DETAILED DESCRIPTION OF THE INVENTION

Figure 1:
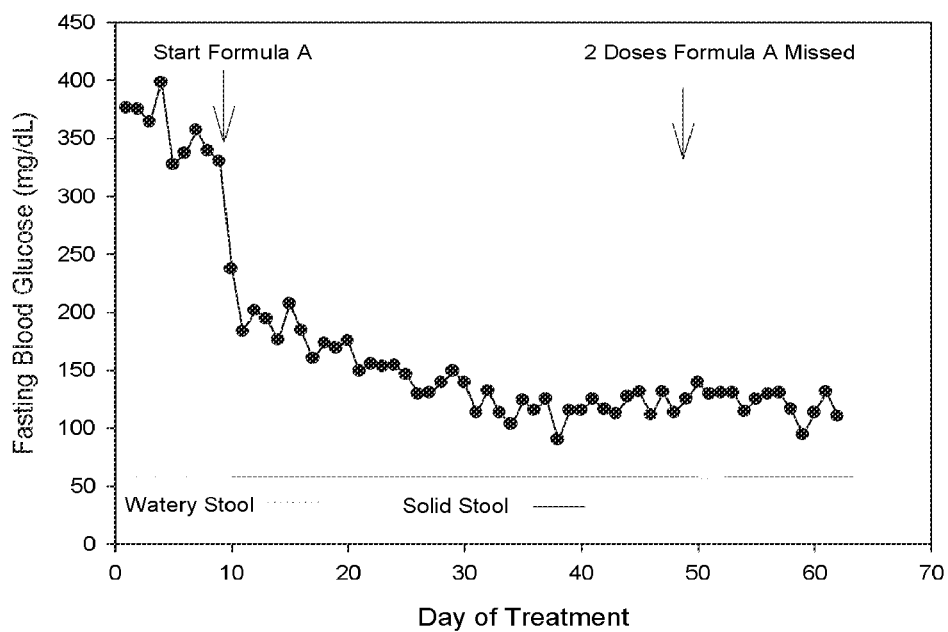
FIG. 1 shows fasting blood glucose levels for 60 days of treatment.

One aspect of the present invention is to include an indigestible carbohydrate such as inulin, oligofructoses, fructo-oligosaccharides, lactulose, galcto-oligosaccharides, xylo-oligosaccharides, resistant starches, in the formula. In addition to offering food for species of Bacteriodetes and selecting for their growth, production of short chain fatty acids (SCFAs) in the colon will suppress pathogenic bacteria and viruses from invading and colonizing the GI tract, partially inhibit hepatic cholesterol biosynthesis, serve as nutrients for colonocytes, reduce colon pH, increase mineral absorption, and serve as ligands to stimulate release of peptide YY (PYY) and glucagon-like peptide-1 (GLP-1) into the blood. PYY and GLP-1 are hormones produced and released from the colon into the blood. PYY signals satiety. GLP-1 stimulates the glucose sensing ability of the insulin secreting cell, prevents that cell from apoptosis, stimulates proliferation of those pancreatic beta cells and inhibits gastric emptying. GLP-1 also stimulates satiety but this may be due to its important role in decreasing gastric emptying.

Ghrelin is a hormone secreted by the stomach that stimulates appetite. Ghrelin is unique because it must be acylated with a medium chain fatty acid (MCFA) on the 3rd residue to bind and trigger its receptor (GHS-R1a) (10). Ghrelin comprised with octanoic (C-8)- or decanoic (C-10)-MCFAs are the most common forms of active ghrelin (10). There are also circulating carboxylesterases that cleave the acyl bond linking the fatty acid to the ghrelin backbone and render ghrelin inactive (11) with respect to appetite and nutrient consumption but may be beneficial for the treatment of T2DM (12). The acylating enzyme in the stomach cell that synthesizes ghrelin was identified about 3 years ago (13,14) and is now a drug target for several groups. The enzyme termed GOAT (ghrelin O-acyltransferase), has a high affinity for MCFAs but can acetylate ghrelin with fatty acids of different lengths. Not only does GOAT prefer MCFAs, but ghrelin that is acylated with a MCFA is much more potent than ghrelin forced to be synthesized with either a small or long chain fatty acid (15). Interestingly, levels of circulating medium chain fatty acids at any time point are relatively low when compared to long chain fatty acids. This is primarily a result of diet. Modern diets and most foods are rich in long chain fatty acids. MCFAs are abundant in coconut oil and human breast milk. Short chain fatty acids (SCFAs) are also rarely in the food chain; they can be found in small quantities in butter and coconut. However, they are produced in large quantities by the microflora in the colon as a byproduct of polysaccharide consumption by the microbiota of the Bacteriodetes division. Recent evidence indicates that GOAT can use a SCFA to acylate ghrelin, rendering the hormone inactive at its receptor (16).

Thus, another novel aspect of the present invention is a formula designed to significantly enhance production of SCFAs by microbiota to serve as substrates for GOAT, render an inactive ghrelin and consequently decrease appetite.

While aspects of the present invention are aimed at increasing the population of colonic microbiota that garners carbohydrates, there is the possibility of those microorganisms redirecting their carbohydrate-harvesting activities from dietary to host polysaccharides according to nutrient availability (7). The colon mucus layer is comprised of mucins, which are glycoproteins that have O-linked oligosaccharides or O-glycans, which account for up to 80% of the mass of mucin (17). This mucus layer covers the gastrointestinal epithelium where it provides a protective layer from the rich intestinal microbiome as well as any pathogens. Such endogenous source of glycans in the microbiome habitat could offer alternative nutrients. However, when dietary glycans are present, it appears that harvesting energy from the diet is preferred (7).

Recently, evidence that bile salts are bacteriostatic to cecal microbiota was presented (24). Moreover, the data indicate that microbiota of the Bacteroidetes phylum are most sensitive to bile salts. Secretion of bile salts into the intestinal tract is stimulated by fat ingestion. Thus, ingestion of fat containing food increases bile secretion, which in turn decreases the numbers of Bacteriodetes microbiota. Viscous beta-glucan encapsulates or sequesters bile acids (25) and thus has the ability to preserve members of the Bacteroidetes, even when fat is ingested.

Thus, an important aspect of the present invention includes dietary glycans. Most are indigestible carbohydrates. Since glycans are also in abundance in yeast walls, one source of dietary glycans is from yeast. Other sources include dietary beta-glucan. Beta-glucan is a natural polysaccharide that can be isolated from oat, barley and wheat most commonly, but also from baker's yeast, certain fungi, mushrooms, and bacteria. Addition of beta-glucan is an important component of the present invention to maintain the mucosa protective barrier as well as to offer nutrients to microbiota that prefer to forage on carbohydrates and would increase the B:F ratio.

Another means to alter an imbalance between microbiota belonging to Bacteroidetes and Firmicutes phyla is to suppress the growth of members of one division. Such bacteriostatic or bactericidal actions for members of Firmicutes division are reported for a number of phenolic compounds that are present in large quantities in berries and other fruits (18). Anthocyanins are the predominating group of phenolic compounds present in berries and are especially abundant (18). A large proportion of dietary polyphenolics remain unabsorbed in the gut lumen where they become concentrated in the ileum and colon. Up to 85% of blueberry anthocyanins enter the colon (19) and appear to exert more growth suppressing effects on members of the Firmicutes division than the Bacteroidetes division (20, 21). Although blueberry powder, blueberry pomace, or blueberry extract containing such polyphenolics is preferred, the present invention preferably includes any fruit or berry ingredient preparation containing similar phenolics such as those listed in Reference 18. The three preferred classes of ingredients, fermentable polysaccharides, beta-glucans, and berry extracts, can be prepared in any type of edible product such as powder to mix in liquid, a bar, smoothie, yogurt, shake, etc. The blend may also be prepared in a capsule or compressed into a tablet. Preferably, the formulation is to be ingested twice per day in between the first and second meals as well as between the second and third meals.

It is preferred that each dose of the formulation contain at least about 4 g of indigestible polysaccharide, at least about 2 g beta-glucan and at least about 4 g of berry powder extract (the equivalent of 2 cups (16 ounces) or 0.47 liters whole blueberries containing about 800 mg of total phenolics, 100 mg of anthocyanins and 6900 μmoles TE antioxidant activity). It is preferred that the dose be administered twice per day within 1 hour prior to meal 1 or within 1 hour prior to meal 2, as well as within 1 hour prior to meal 3. These are our best estimates but the formulation may change.

Ranges of ingredients preferably include about 2-120 mg/kg of body weight of indigestible polysaccharide, about 2-80 mg/kg of body weight of beta-glucan and about 2-120 mg/kg of body weight of blueberry powdered extract or any fruit or berry ingredient preparation containing similar phenolics such as those listed in Reference 18. Ranges of these ingredients more preferably include about 10-80 mg/kg of body weight of indigestible polysaccharide, about 5-50 mg/kg of body weight of beta-glucan and about 10-80 mg/kg of body weight of blueberry powder or any fruit or berry ingredient preparation containing similar phenolics such as those listed in Reference 18. Ranges of these ingredients most preferably include about 20-60 mg/kg of body weight of indigestible polysaccharide that is a fermentable fiber or resistant starch, about 10-30 mg/kg of body weight of beta-glucan and about 20-60-320 mg/kg of body weight of blueberry powdered extract or any fruit or berry ingredient preparation containing similar phenolics such as those listed in Reference 18. One of these ingredients in a formulation is preferable to none, any two are preferable to only one, and most preferably all three are present in a formulation of the present invention that contains less than 70 usable Calories (Cal or kcal) (293 Kilojoules). The calorie or joule content of the formulation can be calculated from derived constants determined for macronutrients in the formula. However, the majority of ingredients in the formula is not digested and absorbed and thus is not assimilated or utilized for energy in the human body. A usable calorie or joule is only the calorie or joule that is assimilated or utilized for energy in the human body.

A preferred indigestible carbohydrate is inulin and can be found naturally in banana, asparagus, garlic, onions and wheat flour at low levels. To consume a sufficient quantity to achieve levels in the most preferred dose is possible but that would contribute significant usable calories or joules to the daily caloric intake of individuals who already have an unhealthy weight (see Table below) because the foods also contains usable calories or joules. Inulin content of raw Jerusalem artichoke, chicory root, and agave is high. Ingestion of a purified preparation of inulin contributes significantly less usable calories or joules to daily caloric intake than does ingestion of a vegetable containing inulin (see Table 1). To obtain the desired dose of inulin by eating the more common vegetable would contribute about 40—times the calories or joules that purified inulin contributes.

TABLE 1

Quantity and Calorie or Kilojoule Content for Preferred Dose of Indigestible Carbohydrate

| Ingredient | Quantity | Calories/Kilojoules |
| --- | --- | --- |
| Purified Inulin | 4 g | 0.48/2.01 |
| Banana | 6 bananas | 630/2,638 |
| Raw Asparagus | 1 cup (0.237 liters) | 27/113 |
| Raw Garlic | 15 cloves | 60/251 |
| Raw Onion | 10 tablespoons chopped | 40/167 |
| Wheat Flour | 1 cup (0.237 liters) | 455/1,905 |
| Raw Jerusalem Artichoke | ¼ cup (0.059 liters) | 18/75 |
| Raw Chicory Root | ½ root | 20/84 |

Beta-glucan can be found naturally in oats, barley, mushrooms and Baker's yeast. To consume a sufficient quantity of these foods to achieve levels in the most preferred dose is possible but that would contribute significant useable calories or joules to the daily caloric intake of individuals who already have an unhealthy weight (see Table 2) because the foods also contains usable calories or joules.

TABLE 2

Quantity and Calorie or Kilojoule Content for Preferred Dose of Beta-Glucan

| Ingredient | Quantity | Calories/Kilojoules |
|---|---|---|
| PromOat Ingredient | 2 g | 5.26/22.02 |
| OatWell 22% | 2 g | 4.3/18.0 |
| Old Fashion Rolled Oats | ½ cup dry (0.118 liters) | 150/628 |
| Barley | ½ cup dry (0.118 liters) | 350/1,465 |
| Shitake Mushrooms | 5 cups pieces (1.18 liters) | 400/1,675 |
| Baker's Yeast | 2 cakes (34 g) | 35.8/149.9 |

Polyphenolics can be divided into major groups of anthocyanidins and flavonoids. They are found naturally in blueberry, cranberry, raspberry, and strawberry. These berries contain different levels of anthocyanidins and flavonoids according to Reference 22 and the abbreviated table below. Blueberries contain the broadest spectrum of polyphenolic compounds. Further, ingestion of the equivalent of 2 cups (16 ounces or 0.47 liters) of fresh blueberries provides sufficient bioactive compounds to improve insulin sensitivity in insulin resistant patients as demonstrated in Reference 23.

TABLE 3

USDA Database for the Anthocyanin Content of Selected Foods, Release 2.1 (2007). Values are the mean in mg/100 g edible portion whole raw berry.

| Cyanidin | Delphinidin | Malvidin | Petunidin |
|---|---|---|---|
| Anthrocyanin - Raw Blueberry | | | |
| 16.97 | 47.40 | 61.35 | 26.42 |
| Anthrocyanin - Raw Cranberry | | | |
| 41.81 | 7.66 | 0.31 | 0 |
| Anthrocyanin - Raw Raspberry | | | |
| 35.84 | 0.29 | 0.70 | 0 |
| Anthrocyanin - Raw Strawberry | | | |
| 1.96 | 0.32 | 0 | 0.08 |

TABLE 4

USDA Database for the Flavonoid Content of Selected Foods, Release 2.1 (2007). Values are the mean in mg/100 g edible portion whole raw berry.

| Epicatechin | Catechin | Myricetin | Quercetin |
|---|---|---|---|
| Flavonoid - Raw Blueberry | | | |
| 13.69 | 37.24 | 2.66 | 5.05 |
| Flavonoid - Raw Cranberry | | | |
| 4.37 | 0.39 | 6.78 | 15.09 |
| Flavonoid - Raw Raspberry | | | |
| 4.07 | 1.56 | 0 | 1.23 |
| Flavonoid - Raw Strawberry | | | |
| 0.12 | 3.32 | 0 | 1.14 |

To consume a sufficient quantity (2 cups (16 ounces) or 0.47 liters) to achieve levels in the most preferred dose of blueberry is possible but that would contribute significant useable calories or joules to the daily caloric intake of individuals who already have an unhealthy weight (see Table 5) because the food also contains usable calories or joules, especially sugar. Pomace is the solid remains of blueberry after pressing for juice and thus removes sugar and water when manufacturing berry juice. Pomace contains indigestible carbohydrate that accounts for 85% of calories or joules. Pomace can be extracted with solvents such as alcohol or water to remove other useable calories. Blueberry extracts of pomace contain less than 10 useable Calories (42 Kilojoules).

TABLE 5

Quantity and Calorie or Kilojoule Content for Preferred Dose of Berry Pomace

| Berry | Calories (kcal)/(kilojoule) Fresh Whole Berry | Calories/Kilojoule Berry Pomace (sugar removed) |
|---|---|---|
| Blueberry (2 cups) (0.47 liters) | 158/662 | 53.2/223 |
| Cranberry (5.38 cups) (1.27 liters) | 323/1,352 | 179.7/752.4 |
| Raspberry (9.41 cups) (2.23 liters) | 602/2,520 | 398/1,666 |
| Strawberry (59.3 cups) (14.03 liters) | 2965/12,414 | 1209.7/5,064.7 |

In some cases dosing may be once a day to initiate treatment and to acclimate the GI microbiome for up to 1 week and then switched to twice daily dosing. In other cases twice daily administration of half the optimal dose is desired such as in children or the elderly. In some cases optimal twice daily dosing may be changed to a daily dosing regimen to maintain the changes stimulated by twice daily dosing. In other cases the twice daily dosing may be switched to twice daily dosing of half the most preferred dose such as in children or adults who cannot tolerate preferred dosing.

The present invention can be used in combination with drugs. For example, broad spectrum antibiotics prescribed for systemic infections are not completely absorbed by the upper GI system and make it to the microbiota environment. This will temporarily alter the GI microbiome and it may be desirable to ingest the formulation of the present invention during antibiotic therapy, in preparation for a course of antibiotics, or following such intervention. Specific antibiotics may target Gram positive or Gram negative bacteria. Treatment with a Gram positive antibiotic before-, during-, or following ingestion of the above combination of prebiotics of the present invention could improve the desired outcome. Because the formulation of the present invention is expected to increase GLP-1 levels, it may be desirable to combine that intervention with a DPP-IV (dipeptidy peptidase type IV) inhibitor such as Vildagliptin, Sitagliptin, or others in this class. This will greatly prolong the half-life of GLP-1 released from the colon and the combination would be preferred over the DPP-IV inhibitor alone or an injection of a GLP-1 peptide agonist such as Byetta. The present invention can also be combined with other diabetes interventions such as biguanides. An example includes metformin (Glucophage, Glucophage X R, Riomet, Fortamet, and Glumetza). In fact, combined use of the present invention with metformin may not only improve blood glucose regulation but will counter the diarrhea side effect often associated with metformin (see Example 5). This is a potentially important clinical observation. Metformin is recommended as the initial drug of choice for the treatment of type-2 diabetes (26). Metformin has been reported to cause a 20% incidence of diarrhea in diabetic patients taking the drug compared to only 6% of diabetic patients not taking metformin (27). In fact, diarrhea with metformin is a sufficient problem that some diabetic patients cannot tolerate the drug. Since metformin has a good safety record, causes an approximate 2-3 kg weight loss and is a low-cost generic medication, increasing the tolerance to metformin while increasing its efficacy using a safe food supplement could have beneficial public health consequences. The present invention may also be combined with alpha-glucosidase inhibitors such as Precose (acarbose) and Glyset (miglitol) that are effective in controlling blood glucose but are poorly tolerated because of associated diarrhea. In addition, some drugs such as atypical antipsychotics and insulin cause weight gain in some patients. The present invention could be combined with such drugs to combat the weight gain without intervening with antipsychotic efficacy.

The present invention can be used to treat other diseases and syndromes. Irritable bowel syndrome (IBS) is a disorder characterized by abdominal pain or discomfort, and altered bowel habit (chronic or recurrent diarrhea, constipation, or both—either mixed or in alternation). IBS with constipation is sometimes referred to as IBS-C or constipation-predominant IBS. IBS with diarrhea is sometimes referred to as IBS-D. The key symptom of IBS is abdominal pain or discomfort anywhere in the abdomen. It may change over time. The impact of IBS can range from mild inconvenience to severe debilitation. Persons with moderate to severe IBS must struggle with symptoms that often impair their physical, emotional, economic, educational and social well-being. The exact cause of IBS is not known. Treatments are available for IBS to help manage symptoms but none appear to address the etiology. Fecal microbiota of patients suffering with IBS have a 2-fold decrease in the ratio of the Bacteroidetes to Firmicutes when compared with healthy individuals (28). Thus, the present invention that stimulates an increase in the ratio of members of the Bacteroidetes phylum to the Firmicutes phylum should be an efficacious and safe therapeutic to treat IBS.

The present invention can be used in preparation for fecal transplant or fecal bacteriotherapy and its follow up. Fecal microbiota transplantation is the process of transplantation of fecal microbiota from a healthy individual into a recipient as a treatment for diseases such as infection by *Clostridium difficile* (29) or more recently, type 2 diabetes (30). Guidelines for both the donor and the recipient are being prepared and will likely indicate strategies for both the donor and the recipient. The use of the present invention in preparation of both subjects for the procedure and continued use by the recipient after transplantation will increase the probability of a successful outcome. The present invention can also be used in preparation for fecal banking. Such practice will permit a subject to prepare a specific fecal sample for banking until needed. This may occur in preparation of prolonged antibiotic surgery, cancer chemotherapy and an unforeseen chronic illness.

The present invention can be used to treat ocular diseases. Recently, it was demonstrated that the microbiota of a conventional raised laboratory mouse adversely alters the ocular lens (31). The present invention is designed to cause a shift in the GI microbiome. Thus, the invention will be useful in prevention of cataracts. Another eye syndrome is commonly called dry-eye syndrome (DES). Traditionally, DES has been thought of as a deficiency of tears at the ocular surface. In recent years, however, investigators have shown that DES is much more complex than previously thought, and that "tear film dysfunction syndrome" might more accurately describe the condition. Tear film dysfunction can be broken down into two basic etiologic classifications: insufficient tear production or increased evaporation of tears from the eye surface (32). The tear film is made up of lipid, aqueous and mucin components. Individuals with dry eye syndrome can be deficient in any of these components and all appear to be related, in part, to healthy GI function. Thus, the present invention will be useful in treating DES.

TABLE 6

Most Preferred Formulation with Function.

| Ingredient | Mass (g/dose) | Function | Reference |
|---|---|---|---|
| Blueberry extract | 4.7 | Weight loss, antimicrobial, antioxidant | 1-5 |
| β-Glucan | 2 | ↑satiety, ↓ LDL chol, ↑PYY, ↑GLP-1 , ↓ ghrelin, ↓ hunger | 6-11 |
| Inulin | 4 | ↑GLP-1, ↑PYY, ↑satiety, ↓ ghrelin, ↓ TG, Support GI Immune System | 12-15 |

↑indicates an increase is reported
↓ indicates that a decrease is reported

TG is triglyceride
1. J. Nutr. 140: 1764-1768, 2010.
2. Chemico-Biological Interactions 189: 1-8, 2011
3. J. Agric. Food Chem. 58: 3970, 2010
4. J Appl Microbiol. 90: 494, 2001
5. Am J Clin Nutr. 79:727, 2004
6. J Med Food 10: 720, 2007
7. Nutr Res 26: 644, 2006.
8. J. Nutr. 138: 732, 2008
9. J Am. Coll. Nutr. 26: 639, 2007.
10. Appetite 53:338, 2009
11. Eur J Clin Nutr 62: 600, 2008.
12. Am J Clin Nutr 89:1751, 2009
13. Appl. Physiol. Nutr. Metab. 35: 9-16 (2010)
14. J. Nutr. 137: 2552S-2556S, 2007
15. J. Nutr. 137: 2547S-2551S, 2007

TABLE 7

Quantity of Ingredients to Formulate Efficacious Doses Containing No More than 70 Useable Calories (293 Kilojoules) (amounts of inulin and beta glucan are pure - quantities of product containing them will be higher):

| Row | Ingredient | Inulin | Beta Glucan from Oat | Blueberry Pomace Extract Powder |
|---|---|---|---|---|
| Row 1 | | | | |
| Row 2 | Alternative | oligofructoses, fructo-oligosaccharides, lactulose, | Beta-glucan from: baker's yeast, | dietary polyphenolic compounds |

TABLE 7-continued

Quantity of Ingredients to Formulate Efficacious Doses Containing No More than 70 Useable Calories (293 Kilojoules) (amounts of inulin and beta glucan are pure - quantities of product containing them will be higher):

| Row | | galacto-oligosaccharides, arabinoxylans, resistant starch, xylo-oligosaccharides, polydextrose, soybean oligosaccharides, isomalto-oligosaccharides, gluco-oligosaccharides, palatinose, gentio-oligosaccharides, lactitol, sorbitol, maltitol, xylitol | oat, barley, wheat, fungi, mushrooms, bacteria, and other biocompatible sources | such as those present in extracts of pomace from berries, grapes, melons |
|---|---|---|---|---|
| Row 3 | Function | Stimulates production of short chain fatty acids in colon, suppress pathogenic bacteria and viruses from colonizing the GI tract, inhibit hepatic cholesterol biosynthesis, provide colonocytes nutrients, reduce colon pH, increase colon mineral absorption, provide ligands to stimulate release of peptide YY (PYY) and glucagon-like peptide-1 (GLP-1) into the blood, produce inactive ghrelin. | Decrease total cholesterol, decrease LDL cholesterol, increase HDL cholesterol, decrease blood glucose, protect intestinal mucosa, prime the GI immune systems, increase viscosity of GI microbiome, absorb excess water in colon. | Inhibit growth of some GI microbiota, induce a reduced intestinal microbiome or serve as an antioxidant, stimulate growth of microbiota that thrive in a reduced environment. |
| Row 4 | Preferred Range | 1-12 g | 0.5-6 g | 1-15 g |
| Row 5 | More Preferred Range | 2-8 g | 0.75-4 g | 2-10 g |
| Row 6 | Most Preferred Range | 3-5 g | 1-3 g | 2-6 g |
| Row 7 | Example | 4 g | 2 g | 4.7 g |

Formula A

FORMULA A is made of 4.7 g dried blueberry pomace extract powder from Milne Fruit Products (Prosser, Wash., product no. FG20155), 9.22 g OatWell 22®beta glucan from CreaNutrition (Sweden), 4.4 g agave inulin (Inufib) from The Iidea Company (Tlaquepaque, Jal., Mexico), with inactive ingredients preferably added for flavor, mouth feel, texture and mixing, including 8.5 g erythritol, 0.5 g soy protein, 0.4 g xanthan gum, 0.38 g citric acid, 0.14 g stevia, and 0.4 g natural flavor that are not believed to affect the efficacy of Formula A. FORMULA A is to be added to a liquid such as 180 ml of water, milk, juice, etc., mixed and consumed as a suspension. The dried blueberry pomace extract powder used in connection with the present invention is preferably blueberry extract powder, product no. FG20155, available from Milne Fruit Products of Prosser, Wash.

Formula A is used in the examples below. One dose of FORMULA A provides 120% of the recommended daily dietary allowance (RDA) of antioxidant activity for children and adults as well as 30% dietary fiber for men and 50% dietary fiber for women, 60% dietary fiber for children aged 1-3, 45% dietary fiber for children aged 4-8, 36% dietary fiber for boys of ages 9-13, and 45% of dietary fiber for girls of ages 9-13.

Preferably a dose of Formula A is taken at least once per day, more preferably at least twice per day, and even more preferably at least 3 times per day. Each dose of FORMULA A is analyzed to contain active and inactive ingredients described in the table 8:

TABLE 8

Active and Inactive Ingredients Measured in the Most Preferred Dose of FORMULA A.

| Analyte | Mass/dose |
|---|---|
| *Active Ingredients* | |
| Total anthrocyanins | 162.53 mg |
| Total polyphenolics | 723.99 mg |
| Antioxidant activity | 6964.4 μmoles TE |
| Beta glucan | 2.03 g |
| Inulin | 3.79 g |
| Other soluble fiber | 3.03 g |
| Insoluble fiber | 2.30 g |
| *Inactive Ingredients* | |
| Protein | 2.87 g |
| Fat | 0.34 g |
| Calcium | 54.81 mg |
| Iron | 1.63 mg |
| Sodium | 52.99 mg |

TABLE 8-continued

Active and Inactive Ingredients Measured
in the Most Preferred Dose of FORMULA A.

| Analyte | Mass/dose |
| --- | --- |
| Potassium | 132.32 mg |
| Erythritol | 8.39 g |
| Sucrose | 0.17 g |
| Fructose | 1.54 g |
| Glucose & Galactose | 0.71 g |

Further analysis of the phenolic content of FORMULA A is described by the table 9:

TABLE 9

Finger Print Analysis of Polyphenolics Present
in the Most Preferred Dose of Formula A.

| Catechins[1] | |
| --- | --- |
| Epigallocatechin Gallate | 158.2 mg |
| Epicatechin Gallate | 110.5 mg |
| Epigallocatechin | 21.9 mg |
| Catechin | 6.7 mg |
| Epicathecin | 3.5 mg |
| Quercetin | 3.2 mg |
| Gallocatechin Gallate | 1.1 mg |
| Gallocatechin | ND |
| Catechin Gallate | ND |
| Anthocyanins[1] | |
| Malvidin 3-O-Galactoside | 30.9 mg |
| Malvidin 3-O-Arabinoside | 17.7 mg |
| Malvidin 3-O-Glucoside | 12.4 mg |
| Delphinidin 3-O-Arabinoside | 9.4 mg |
| Delphinidin 3-O-Galactoside | 7.5 mg |
| Petunidin 3-O-Galactoside | 6.8 mg |
| Petunidin 3-O-Arabinoside | 6.4 mg |
| Petunidin 3-O-Glucoside | 5.0 mg |
| Delphinidin 3-O-Glucoside | 4.5 mg |
| Peonidin Chloride | 1.5 mg |
| Cyanidin 3-O-Arabinoside | 1.2 mg |
| Peonidin 3-O-Glucoside | 1.2 mg |
| Cyanidin 3-O-Glucoside | 0.7 mg |
| Delphinidin Chloride | 0.6 mg |
| Peonidin 3-O-Arabinoside | 0.5 mg |
| Peonidin 3-O-Galactoside | 0.4 mg |
| Petunidin Chloride | 0.4 mg |
| Cyanidin Chloride | 0.4 mg |
| Cyanidin 3-O-Galactoside | ND |
| Cyanidin 3-O-Rutinoside | ND |
| Malvidin Chloride | ND |

[1]HPLC analysis,
[2]ORAC trolox equivalents,
ND = not detectable

Example 1

Human Study Utilizing FORMULA A to Increase the Ratio of Gastrointestinal Microbiota in Phylum Bacteroidetes to Microbiota of Firmicutes Phylum, Improve Glucose Regulation and Improve Body Composition Subject and Methods a) The required number of subjects are properly screened to fulfill the necessary qualifications,
b) appropriate laboratory evaluations are performed,
c) measures of positive primary and secondary outcome responses are recorded,
d) adverse events are documented, and
e) patients are adequately followed-up.

Overview

This study is expected to demonstrate that overweight subjects with impaired fasting blood glucose on an ad libitum diet who take formula A either within 1 hour prior to meal 1 or within 1 hour prior to meal 2, as well as within 1 hour prior to meal 3 for 4 weeks:

1. Eliminate stool containing a greater ratio of microbiota species from the Bacteroidetes phylum to Firmicutes phylum than this ratio of microbiota in their stool at the start of the intervention, and when compared to subjects consuming a placebo, and 2. Have an improved oral glucose tolerance test (OGTT) as measured by blood glucose and insulin levels before, during, and at 120 minutes after ingestion of 75 g glucose when compared to their initial OGTT, and when compared to subjects consuming placebo, and 3. Have lower overnight fasting blood glucose levels as measured by a blood glucose monitor before ingesting a morning meal when compared to their overnight fasting blood glucose values at the start of the intervention, and when compared to subjects consuming placebo.

4. Experience an improved body composition as measured by a decrease in body weight, a decrease in body fat or % body fat, a decrease in waist circumference measurements, and 5. Experience decreased appetite before a meal, increased satiety during the meal, when compared to subjects consuming placebo, and 6. are found to have elevated GLP-1 as well as PYY levels with reduced active ghrelin levels after a standardized meal when the values are compared to those of subjects consuming placebo on week 3 of the intervention.

General

In this study, subjects consume either 180 ml of FORMULA A formula or a placebo containing the same total dietary fiber level as FORMULA A but as inactive cellulose orally within 1 hour prior to consumption of either meal 1 or meal 2 and within 1 hour prior to consumption of meal 3 each day. Placebo formula contains cellulose with food coloring and flavor to match the total dietary fiber content (8.75 g) of FORMULA A. Placebo is prepared by Merlin Development at the same time they prepare FORMULA A Subjects report weekly for measurements and assessment of any side effects. They are asked to collect a stool sample before initiating either FORMULA A or placebo intervention as well as at the end of the 4 week treatment period. They are also asked to record any side effects and their frequency (checklist assessment). They are asked to record appetite (how hungry are you) and satiety (how full are you) during the standardized meal at the 3rd week of intervention. They are provided with the proper paper work to record these.

Subject Screening and Selection

A total of 30 subjects is selected, 15 assigned to FORMULA A and 15 assigned to placebo.

QUALIFICATIONS OF SUBJECTS 1) Healthy men and women between the ages of 18 and 70 with a BMI between 25 and 35 are eligible. 2) Fasting blood glucose between 100 and 125 mg/dl. 3) Stable weight over 2 months Subjects Excluded from the Study People who:
a) take medications affecting glucose,
b) take medications affecting insulin,
c) take medications affecting body weight,
d) take medications affecting bacterial flora,
e) have intestinal disease or a recent history of intestinal disease,
f) have had surgery on stomach or intestine,
g) are hypothyroid, h) are pregnant,
i) have heart disease.

Appropriate Laboratory Evaluation

Different tests are performed at the screening of potential participants, at the beginning of the study, and at the end of the 4 week treatment period.

1) SCREENING: Subjects are screened to exclude hypothyroidism, pregnancy, and heart disease. The following tests can suffice for this: T4 (thyroxin), T3 (triiodotyronine), TSH (thyroid stimulating hormone), urine pregnancy test, blood pressure & ECG (electrocardiogram).

2) BEGINNING OF STUDY: Subjects passing the initial screen are evaluated at the beginning of WEEK #1 as follows:
   a) Fasting blood glucose and insulin levels.
   b) SMA 20 (Sequential multi-channel analysis with computer-20, a metabolic panel with 20 different analytes), including, uric acid, and liver function tests
   c) Triglycerides
   d) Cholesterol, including fractions
   e) Glycosylated hemoglobin A1 (HgbA1)
   f) Weight, taken on the same scale each time
   g) Body fat % and total body fat, determined by DXA (dual-energy X-ray absorptiometry).
   h) Height
   i) Waist and hip measurements
   j) Blood glucose, insulin, GLP-1, PYY and ghrelin responses to a 75 g oral glucose challenge
   k) Assessment of appetite and satiety using a visual analog scale
   l) Stool is collected and stored frozen but not analyzed until the end of study.

3) END OF STUDY ASSESSMENT:
   a) all labs and assessments done in step 2 at beginning of study,
   b) Analysis of the fecal microbiome DNA from both the initial sample and the final sample.

STUDY DESIGN

Subjects selected for participation are allowed an ad libitum diet and are given an evaluation sheet to assess their appetite and satiety before and after a meal. Foods excluded include alcohol. Low calorie or joule liquids are stressed in place of high calorie or joule liquids such as fruit juices, milk, sweet tea (tea with sugar), regular soft drinks, coffee with sugar, etc. The subjects are randomly assigned to either FORMULA A or placebo treatments. Both the experimenter and the subjects are blinded to who receive FORMULA A or the placebo. The subjects are encouraged to consume either treatment within 1 hour prior to either breakfast or lunch and within 1 hour prior to dinner.

DURATION

Subjects are given a 4 weeks supply of either FORMULA A or placebo at the onset and are instructed to consume the entire 180 ml volume within 1 hour prior to either meals 1 or 2, as well as another 180 ml volume containing either FORMULA A or placebo within 1 hour prior to meal 3. Ad libitum diets are followed for 4 weeks, but the volunteers are instructed to consume either FORMULA A or placebo as their only between meal snack.

OUTCOME

This study is expected to demonstrate that FORMULA A:

1) Increases the ratio Bacteroidetes species to Firmicutes species in fecal samples when samples at the end of study are compared to samples at the onset of study; and when the ratio of species is compared to samples from the placebo group
2) Improves the blood glucose and insulin responses to an OGTT by decreasing the areas under the insulin curve (improved insulin sensitivity);
3) Decrease fasting blood glucose values
4) Produces weight loss, loss of body fat, and (or) decrease of body fat %
5) Increases GLP-1 and PYY response to the oral glucose challenge and decreases the fasting ghrelin levels at 1 hour after the both the OGTT and the standardized meal when comparing final values to the initial measurements of the OGTT, and when comparing to those findings of the placebo group during the standardized meal; and
6) Decreases stool pH;
7) Increases stool SCFA.

If subjects took FORMULA A for periods longer than 4 weeks, particularly for at least 8 weeks, the subjects would experience significant weight loss that was primarily fat loss.

Example 2

Human Study Utilizing either FORMULA A or a Placebo Snack Replacement to Increase the Ratio of Gastrointestinal Microbiota in Phylum Bacteroidetes to Microbiota of Firmicutes Phylum, Improve Glucose Regulation and Improve Body Composition Subject and Methods a) The required number of subjects are properly screened to fulfill the necessary qualifications,
b) appropriate laboratory evaluations are performed,
c) measures of positive primary and secondary outcome responses are recorded,
d) adverse events are documented, and
e) patients are adequately followed-up.

Overview

This study is expected to demonstrate that overweight subjects with impaired fasting blood glucose on an ad libitum diet who take FORMULA A, but not those assigned to consume a placebo, within 2 hours prior to consuming either meal 1 or meal 2, as well as within 2 hours prior to consuming meal 3 as a snack replacement for 4 weeks:

1. Eliminate stool containing a greater ratio of microbiota species from the Bacteroidetes phylum to Firmicutes phylum than this ratio of microbiota in their stool at the start of the intervention, and
2. Have an improved oral glucose tolerance test (OGTT) as measured by blood glucose and insulin levels before, during, and at 120 minutes after ingestion of 75 g glucose when compared to their initial OGTT, and
3. Experience an improved body composition as measured by a decrease in body weight, a decrease in body fat or % body fat, a decrease in waist circumference measurements, and
4. Experience lower fasting blood glucose levels when compared to either the initial values or those of the placebo group, and
5. Experience decreased appetite before a meal, increased satiety during the meal, and 6. are found to have elevated GLP-1 as well as PYY levels with reduced active ghrelin levels at 1 hour after both the OGTT and the standardized meal when the values are compared to those at the initiation of the trial (OGTT) or the placebo group (standardized meal test).

General

In this study, subjects are randomly selected to consume 180 ml of either FORMULA A formula or placebo formula orally within 2 hours prior to ingestion of either meals 1 or 2 as well as within 2 hours prior to consumption of meal 3 each day. The subjects and experiments are blinded to the treatment assignments. Placebo formula contains cellulose with food coloring and flavor to match the total dietary fiber content (8.75 g) of FORMULA A. Placebo is prepared by Merlin Development at the same time they prepare FORMULA A. Both formulations are coded by Merlin Development and the code is maintained with them as well as is held in confidence by a pharmacist at the study clinic until all data are collected at the end of study.

Subjects report weekly for measurement s and assessment of any side effects. They are asked to collect a stool sample before initiating FORMULA A or Placebo intervention as well as at the end of the 4 week treatment period. They are also asked to record any side effects and their frequency (checklist assessment). They are asked to record appetite (how hungry are you) and satiety (how full are you) during the OGTT at both the onset and at the end of the trial as well as during a 3$^{rd}$ standardized meal. They are provided with the proper paper work to record these.

Subject Screening and Selection

A total of 30 subjects is selected. Fifteen subjects are randomly assigned to consume FORMULA A and the remaining 15 subjects are assigned to the FORMULA A group. The demographics of each group are carefully matched.

QUALIFICATIONS OF SUBJECTS 1) Healthy men and women between the ages of 18 and 70 with a BMI between 25 and 35 are eligible. 2) Fasting blood glucose between 100 and 125 mg/dl. 3) Stable weight over 2 months.

Subjects Excluded from the Study

People who:
a) take medications affecting glucose,
b) take medications affecting insulin,
c) take medications affecting body weight,
d) take medications affecting bacterial flora,
e) have intestinal disease or a recent history of intestinal disease,
f) have had surgery on stomach or intestine,
g) are hypothyroid,
h) are pregnant,
i) have heart disease.

Appropriate Laboratory Evaluation

Different tests are performed at the screening of potential participants, at the beginning of the study, and at the end of the 4 week treatment period.
4) SCREENING: Subjects are screened to exclude hypothyroidism, pregnancy, and heart disease. The following tests can suffice for this: T4 (thyroxin), T3 (triiodotyronine), TSH (thyroid stimulating hormone), urine pregnancy test, blood pressure & ECG (electrocardiogram).
5) BEGINNING OF STUDY: Subjects passing the initial screen are evaluated at the beginning of WEEK #1 as follows:
   a) Fasting blood glucose and insulin levels.
   b) SMA 20 (Sequential multi-channel analysis with computer-20, a metabolic panel with 20 different analytes), including, uric acid, and liver function tests
   c) Triglycerides
   d) Cholesterol, including fractions
   e) Glycosylated hemoglobin A1 (HgbA1)
   f) Weight, taken on the same scale each time
   g) Body fat % and total body fat, determined by DXA (dual-energy X-ray absorptiometry).
   h) Height
   i) Waist and hip measurements
   j) Blood glucose, insulin, GLP-1, PYY and ghrelin responses to a 75 g oral glucose challenge
   k) Assessment of appetite and satiety using a visual analog scale
   l) Stool is collected and stored frozen but not analyzed until the end of study.
6) END OF STUDY ASSESSMENT:
   c) all labs and assessments done in step 2 at beginning of study,
   d) Analysis of the fecal microbiome DNA from both the initial sample and the final sample.

STUDY DESIGN

Subjects selected for participation are allowed an ad libitum diet and are given an evaluation sheet to assess their appetite and satiety before and after a meal.

Foods excluded include alcohol. Low calorie or joule liquids are stressed in place of high calorie or joule liquids such as fruit juices, milk, sweet tea (tea with sugar), regular soft drinks, coffee with sugar, etc. The subjects are encouraged to consume either FORMULA A or Placebo as their only between meal snack.

DURATION

Subjects are given a 4 weeks supply of ether FORMULA A or Placebo at the onset and are instructed to consume the entire 180 ml volume containing either formula within 2 hours prior to either meals 1 or 2, as well as another 180 ml volume containing either formula within 2 hours prior to meal 3. Ad libitum diets are followed for 4 weeks, but the volunteers are instructed to consume either FORMULA A or Placebo as their only between meal snack.

OUTCOME

This study is expected to demonstrate that FORMULA A and not Placebo:
1) Increases the ratio of Bacteroidetes species to Firmicutes species in fecal samples when samples at the end of study are compared to samples at the onset of study;
2) Improves the blood glucose and insulin responses to an OGTT by decreasing the areas under the insulin curve (improved insulin sensitivity);
3) produces weight loss, loss of body fat, and (or) decrease of body fat %;
4) Increases GLP-1 and PYY response to the oral glucose challenge and decreases the fasting ghrelin levels prior to the OGTT when comparing final values to the initial measurements;
5) Decreases stool pH;
6) Increases stool SCFA.

If subjects took FORMULA A as a snack replacement for periods longer than 4 weeks, particularly for at least 8 weeks, the subjects would experience significant weight loss that was primarily fat loss.

Example 3

Human Study Utilizing FORMULA A in Combination with an Inhibitor of Dipeptidyl peptidase-4 (DPP-4) to Increase the Ratio of Gastrointestinal Microbiota in Phylum Bacteroidetes to Microbiota of Firmicutes Phylum and Improve Glucose Regulation by Sustained Elevation of GLP-1

Subject and Methods
a) The required number of subjects are properly screened to fulfill the necessary qualifications,
b) appropriate laboratory evaluations are performed,
c) measures of positive primary and secondary outcome responses are recorded,
d) adverse events are documented, and
e) patients are adequately followed-up.

Overview

This study is expected to demonstrate that Type 2 diabetic (T2D) subjects with insulin resistance on an ad libitum diet who take a DPP-4 inhibitor and FORMULA A within 1 hour prior to either meal 1 or meal 2, as well as within 1 hour prior to meal 3 for 4 weeks:

1. Eliminate stool containing a greater ratio of microbiota species from the Bacteroidetes phylum to Firmicutes phylum than this ratio of microbiota in their stool at the start of the intervention and when compared to those only taking the DPP-4 inhibitor, and 2. Have improved insulin sensitivity when compared to both initiation of the study and when compared to those only taking a DPP-4 inhibitor. Insulin sensitivity is measured by an oral glucose tolerance test (OGTT). This is performed by measuring blood glucose and insulin levels before, during, and at 120 minutes after ingestion of 75 g glucose when compared to their initial OGTT, and 3. Have improved fasting blood glucose values when compared to those only taking the DPP-4 inhibitor, and 4. experience an improved body composition as measured by a decrease in body weight, a decrease in body fat or % body fat, a decrease in waist circumference measurements when compared to their baseline values and when compared to those only taking the DPP-4 inhibitor, and 5. experience decreased appetite before a standarized meal, increased satiety during that meal when compared to their baseline values and when compared to those only taking the DPP-4 inhibitor, and 6. are found to have elevated GLP-1 as well as PYY levels with reduced ghrelin levels at 1 hour after the both the OGTT and the standardized meal when the values are compared to their baseline values and when compared to those only taking the DPP-4 inhibitor.

General

In this study, T2D patients are randomly assigned to either consume 180 ml of FORMULA A or a placebo formula containing cellulose orally within 1 hour prior to either meals 1 or 2 as well as within 1 hour prior to meal 3 each day. Patients and experimenters are blinded to this assignment. All patients are also instructed to take sitagliptin (Januvia®) at the recommended dose of 100 mg, once per day in the morning prior to meal 1 as a treatment to manage their diabetes.

Subjects report weekly for measurements and assessment of any side effects. They are asked to collect a stool sample before the initiation of the trial as well as at the end of the 4 week treatment period. They are also asked to record any side effects and their frequency (checklist assessment). They are asked to record appetite (how hungry are you) and satiety (how full are you) during the OGTT at both the onset and at the end of the trial as well as before and during a standardized meal at the $3^{rd}$ week of treatments. They are provided with the proper paper work to record these.

Subject Screening and Selection

A total of 24 subjects is selected. 12 will be randomly assigned to receive Januvia®+placebo (a cellulose solution that contains the same total dietary fiber content as FORMULA A and mimics FORMULA A in color and taste) or Januvia®+FORMULA A.

QUALIFICATIONS OF SUBJECTS 1) T2D men and women between the ages of 18 and 70 with a BMI between 25 and 35 are eligible. 2) Fasting blood glucose between greater than 125 mg/dl. 3) Stable weight over 2 months Subjects Excluded from the Study People who:
a) take medications affecting glucose other than Januvia,
b) take medications affecting insulin other than Januvia,
c) take medications affecting body weight,
d) take medications affecting bacterial flora,
e) have intestinal disease or a recent history of intestinal disease,
f) have had surgery on stomach or intestine,
g) are hypothyroid,
h) are pregnant,
i) have heart disease.

Appropriate Laboratory Evaluation

Different tests are performed at the screening of potential participants, at the beginning of the study, and at the end of the 4 week treatment period.

(7) SCREENING Subjects are screened to exclude hypothyroidism, pregnancy, and heart disease. The following tests can suffice for this: T4, T3, TSH, urine pregnancy test, blood pressure & ECG. Fasting blood glucose, fasting insulin and HgbA1 levels are also measure as an assessment of their diabetic state.

(8) BEGINNING OF STUDY: Subjects passing the initial screen are evaluated at the beginning of WEEK #1 as follows:
   a) Fasting blood glucose, insulin, and HgbA1 levels.
   b) SMA 20, including uric acid and liver function tests
   c) Triglycerides
   d) Cholesterol, including fractions
   f) Weight, taken on the same scale each time
   g) Body fat % and total body fat, determined by DXA,
   h) Height
   i) Waist and hip measurements
   j) Blood glucose, insulin, GLP-I, PYY and ghrelin responses to a 75 g oral glucose challenge
   k) Assessment of appetite and satiety before, during and after a standardized meal using a visual analog scale
   l) Stool is collected and stored frozen but not analyzed until the end of study.

(9) END OF STUDY ASSESSMENT:
   e) all labs and assessments done in step 2 at beginning of study,
   f) Analysis of the fecal microbiome DNA from both the initial sample and the final sample.

STUDY DESIGN

Patients selected for participation are allowed an ad libitum diet and are given an evaluation sheet to assess their appetite and satiety. Foods excluded include alcohol. Low calorie or joule liquids are stressed in place of high calorie or joule liquids such as fruit juices, milk, sweet tea (tea with sugar), regular soft drinks, coffee with sugar, etc. All 24 patients are also instructed to take sitagliptin (Januvia®) at the recommended dose of 100 mg, once per day in the morning with or without food as a treatment to manage their diabetes. 12 patients are randomly selected to also consume FORMULA A before 2 of 3 daily meals and the remaining 12 patients are instructed to consume a placebo before 2 of 3 daily meals. Patients and investigators are blinded to whether the snack replacement is placebo or FORMULA A.

DURATION

Subjects are given a 4 weeks supply of sitagliptin and either FORMULA A or placebo at the onset and are instructed to consume the entire 180 ml volume of either snack replacement within 1 hour prior to either meals 1 or 2, as well as another 180 ml volume of snack replacement within 1 hour prior to meal 3. All subjects are required to take 1 tablet of sitagliptin daily (100 mg) in the morning with or without food. Ad libitum diets are followed for 4 weeks.

OUTCOME

This study is expected to demonstrate that FORMULA A:

1) Increases the ratio of Bacteroidetes species to Firmicutes species in fecal samples when samples at the end of study from those assigned to FORMULA A are compared to samples at the onset of study and when subjects taking Januvia+FORMULA A are compared to patients taking Januvia+placebo.
2) Improves the blood glucose and insulin responses to an OGTT by decreasing the areas under the insulin curve (improved insulin sensitivity) when subjects taking Januvia+FORMULA A are compared to patients taking Januvia+placebo
3) produces weight loss, loss of body fat, and (or) decrease of body fat % when patients assigned to FORMULA A are compared to samples at the onset of study and when subjects taking Januvia+FORMULA A are compared to patients taking Januvia+placebo.
4) produces decreased fasting blood glucose levels when subjects taking Januvia+FORMULA A are compared to patients taking Januvia+placebo, and
5) Increases GLP-1 and PYY response to the oral glucose challenge and decreases the fasting ghrelin levels prior to the OGTT when patients assigned to FORMULA A are compared to samples at the onset of study and when subjects taking Januvia+FORMULA A are compared to patients taking Januvia+placebo,
6) Decreases stool pH when patients assigned to the FORMULA A arm are compared to samples at the onset of study and when subjects taking Januvia+FORMULA A are compared to patients taking Januvia+placebo
7) Increases stool SCFA when patients assigned to the FORMULA A arm are compared to samples at the onset of study and when subjects taking Januvia+FORMULA A are compared to patients taking Januvia+placebo If subjects took FORMULA A with other DPP-IV inhibitors or other formulations of Januvia, the subjects are expected to also have significantly improved glucose regulation.

Example 4

Study Utilizing FORMULA A Snack Replacement to Increase the Ratio of Gastrointestinal Microbiota in Phylum Bacteroidetes to Microbiota of Firmicutes Phylum, Improve Glucose Regulation and Improve Body Composition in Overweight Children Subject and Methods a) The required number of children are properly screened to fulfill the necessary qualifications and their parental consent is obtained,
b) appropriate laboratory evaluations are performed,
c) measures of positive primary and secondary outcome responses are recorded,
d) adverse events are documented, and
e) children and their parents are adequately followed-up.

Overview

This study is expected to demonstrate that overweight children with prediabetes or at high risk of developing T2D (type 2 diabetes) on an ad libitum diet who take FORMULA B (identical active ingredients to FORMULA A but formulated in a child friendly delivery system such as ice cream, jelled animals, cookies, etc.) within 1 hour prior to either meal 1 or meal 2, as well as within 1 hour prior to meal 3 for 4 weeks:

1. Eliminate stool containing a greater ratio of microbiota species from the Bacteroidetes phylum to Firmicutes phylum than this ratio in their stool at the start of the intervention, and
2. Have an improved oral glucose tolerance test (OGTT) as measured by blood glucose and insulin levels before, during, and at 120 minutes after ingestion of 1.75 g glucose/kg body weight up to 75 g glucose when compared to their initial OGTT, and
3. experience an improved body composition as measured by a decrease in body weight, a decrease in body fat or % body fat, a decrease in waist circumference measurements, and
4. Experience decreased fasting blood glucose levels
5. experience decreased appetite before a meal, increased satiety during the meal, and
6. are found to have elevated GLP-1 as well as PYY levels with reduced ghrelin levels 1 hour after the OGTT when the values are compared to those at the initiation of the trial.

General

In this study, children consume 6 jelled animals of FORMULA B formula (each jelled animal contains about 20 g of FORMULA B) within 1 hour prior to either meals 1 or 2 as well as within 1 hour prior to meal 3 each day.

Subjects report weekly for measurements and assessment of any side effects. They are asked to collect a stool sample before initiating FORMULA B intervention as well as at the end of the 4 week treatment period. They are also asked to report side effects to their parents who record them and their frequency (checklist assessment). The parents are instructed to ask and to record appetite (how hungry are you) and satiety (how full are you) before, during, and after a standardized $3^{rd}$ meal at the beginning of study and at the end. The investigators score the same assessment during the OGTT at both the onset and at the end of the trial as well as at home. The parents are provided with the proper paper work to record these.

Subject Screening and Selection

A total of 10 children is selected.

QUALIFICATIONS OF SUBJECTS 1) Healthy prepubertal boys and girls between the ages of 7 and 12 with a BMI between 25 and 30 are eligible. 2) Fasting blood glucose between 100 and 125 mg/dl.

Subjects Excluded from the Study

Children who:
a) take medications affecting glucose,
b) take medications affecting insulin,
c) take medications affecting body weight,
d) take medications affecting bacterial flora,
e) have intestinal disease or a recent history of intestinal disease,
f) have had surgery on stomach or intestine,
g) are hypothyroid, Appropriate Laboratory Evaluation Different tests are performed at the screening of potential participants, at the beginning of the study, and at the end of the 4 week treatment period.

Screening:

Children are screened to exclude hypothyroidism and puberty. The following tests can suffice for this: T4, T3, TSH, a physical exam, and in questionable cases based on the physical exam or peripubertal presentations, a gonadotropin-releasing hormone challenge test.

Beginning of Study:

Children passing the initial screen are evaluated at the beginning of WEEK #1 as follows:
a) Fasting blood glucose and insulin levels.
b) SMA 20, including uric acid and liver function tests
c) Triglycerides
d) Cholesterol, including fractions
e) Glycosylated hemoglobin A1 (HgbA1)
f) Weight, taken on the same scale each time
g) Body fat % and total body fat, determined by DXA.
h) Height
i) Waist and hip measurements
j) Blood glucose, insulin, GLP-I PYY and ghrelin responses to a 1.75 g/kg (up to 75 g) oral glucose challenge
k) Assessment of appetite and satiety using a visual analog scale
(l) Stool is collected and stored frozen but not analyzed until the end of study.

End of Study Assessment:
a) all labs and assessments done in step 2 at beginning of study,
b) Analysis of the fecal microbiome DNA from both the initial sample and the final sample.

STUDY DESIGN

Children selected for participation are allowed an ad libitum diet and their parents are given an evaluation sheet to assess their appetite and satiety. Low calorie or joule liquids are stressed in place of high calorie or joule liquids such as fruit juices, milk, regular soft drinks, coffee with sugar, etc. The children are encouraged to consume FORMULA B as their only between meal snack. Other snacks such as candy, ice cream, milk shakes, cookies, potato chips, etc. are discouraged.

DURATION

Children are given a 4 weeks supply of FORMULA B at the onset and are instructed to consume the entire 6 jelled animals containing FORMULA B within 1 hour prior to either meal 1 or 2, as well as another 6 jelled animals containing FORMULA B within 1 hour prior to meal 3. Ad libitum diets are followed for 4 weeks, but the children are instructed to consume FORMULA B as their only between meal snack.

OUTCOME

This study is expected to demonstrate that FORMULA B:
1) Increases the ratio of Bacteroidetes species to Firmicutes species in fecal samples when samples at the end of study are compared to samples at the onset of study.
2) Improves the blood glucose and insulin responses to an OGTT by decreasing the areas under the insulin curve (improved insulin sensitivity)
3) produces weight loss, loss of body fat, and (or) decrease of body fat %
4) Increases GLP-1 and PYY response to the oral glucose challenge and decreases the fasting ghrelin levels prior to the OGTT when comparing final values to the initial measurements.
5) Decreases stool pH
6) Increases stool SCFA If children took FORMULA A for periods longer than 4 weeks as a snack replacement, particularly for at least 8 weeks, the children would experience significant weight loss that was primarily fat loss.

Example 5

Formula A Augments the Efficacy and Gatrointestinal Tolerability of Metformin: A Case Report Subject JH was a 30 year old Caucasian male who gained 10 kg over the course of 8 months and developed lower back pain. He presented to his primary physician with that complaint.

The patient was taking omeprazole (20 mg/d), lisinopril (40 mg/d), metoprolol (100 mg/d), and hydrochlorothiazide (25 mg/d) at the time of his presentation, had no allergies and had undergone no surgeries. He denied past hospitalizations, trauma with residua or blood transfusions. He had never smoked, drank 3-4 alcoholic drinks per week on average and had no history of intravenous drug use. He was a full-time law student and had no exposures to occupational toxins. During the 6 months prior to his presentation he had been sexually active with one woman. The patient's mother and father were living and well. He had one sister who was living and well, and he had no children. There was no family history of diabetes. He had no complaint other than lower back pain. On physical examination he was 104 kg with a height of 165 cm and a body mass index (BMI) of 38.3 kg/m$^2$. His blood pressure was 116/70 with a pulse rate of 80/min and he was afebrile. Urinalysis demonstrated presence of glucose, that was followed up by a non-fasting capillary blood glucose of 450 mg/dl glucose and a hemoglobin A1c of 8.8% and a microalbumin/creatine ratio of 147. His physician made the diagnosis of type 2 diabetes mellitus based on his age, lack of acidosis and a fasting blood sugar of 375 mg/dL. He was started on metformin 500 mg twice a day and was instructed to measure his fasting blood sugar on a daily basis. Over the course of 7 days he was instructed to increase metformin to 1000 mg twice a day. Over the course of the next 9 days he developed persistent watery stools and his fasting blood sugar decreased to about 325 mg/dL. He knew from his contact with NuMe Health, LLC that the company was developing and testing a dietary supplement with a goal of increase insulin sensitivity through a salutary effect on the stool microbiome. On the 9th day of his treatment with 1000 mg metformin dose, he added FORMULA A taken twice a day within an hour before breakfast or lunch and within an hour before dinner. Within two days of starting FORMULA A his fasting glucose dropped from 325 mg/dL to 175 mg/dL and after 5 weeks of taking the FORMULA A along with the metformin, his fasting blood glucose was 100 mg/dL (FIG. 1).

FIG. 1 shows fasting blood glucose levels at the start of 1000 mg metformin twice daily. Formula A was added twice daily on day 9 and the combination was continued except from days 49 to 51 when daily dosing of FORMULA A was missed. Diarrhea was associated with metformin except when Formula A was added.

Figure 2:
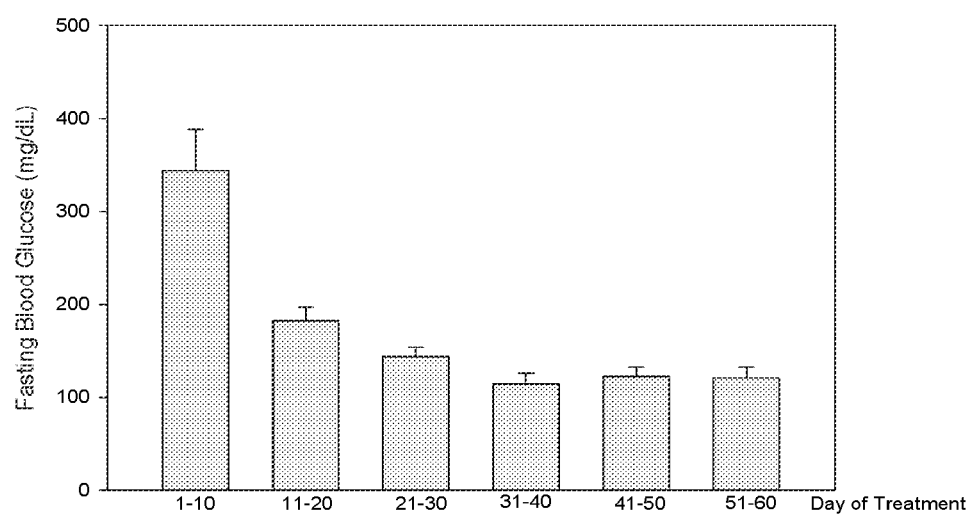
FIG. 2 shows fasting blood glucose levels for 60 days of treatment divided into 10 day periods.

Dividing the first 60 days of diabetes treatment into 10 day periods, his blood sugar and its variance (standard deviation) decreased from 344±44.1 mg/dL in the first 10 days, to 182.2±14.7 in the second 10 days, 144.3±9.6 during the third 10 days, 114.5±11.8 during the fourth 10 days, 123.0±9.6 during the fifth 10 days, and 121.0±11.8 during the sixth 10 days (FIG. 2).

During this period, his weight decreased by 5.5 kg, and his watery stools reverted to soft regular formed bowel movements. After an additional month, he ran out of his FORMULA A for 2 days. During that period, his blood sugar increased from 100 mg/dL to 131 mg/dL and his diarrhea returned. After resuming FORMULA A his blood sugar returned to 113 mg/dL and his stools return to being formed and soft. His diabetic control and stools have remained under control on the combination of metformin and FORMULA A at the time of this writing and he has lost about 5.5 kg body weight. His hemoglobin A1c decreased to 6.3% and a microalbumin/creatine ratio was 16.

Discussion

This case report is encouraging. Not only did FORMULA A appear to have a positive effect on fasting blood sugar, but the watery stools induced by treatment with metformin were normalized. This is a potentially important clinical observation. Metformin has been recommended as the initial drug of choice for the treatment of type-2 diabetes (26). Metformin has been reported to cause a 20% incidence of diarrhea in diabetic patients taking the drug compared to only 6% of diabetic patients not taking metformin (27). In fact, diarrhea with metformin is a sufficient problem that some diabetic patients cannot tolerate the drug. Since metformin has a good safety record, causes an approximate 2-3 kg weight loss and is a low-cost generic medication, increasing the tolerance to metformin while increasing its efficacy using a safe food supplement could have beneficial public health consequences.

Acarbose is another drug used to treat diabetes that is associated with the side effect of a watery stool because of its mechanisms of action. If FORMULA A is used in conjunction with acarbose to treat type 2 diabetes, both better control of blood glucose and solid stool formation are expected.

Example 6

Human Study Utilizing either FORMULA A or a Placebo to Increase the Ratio of Gastrointestinal Microbiota in Phylum Bacteroidetes to Microbiota of Firmicutes Phylum and Improve Symptoms of Irritable Bowel Syndrome (IBS)

Subject and Methods a) The required number of subjects are properly screened to fulfill the necessary qualifications,
b) appropriate laboratory evaluations are performed,
c) measures of positive primary and secondary outcome responses are recorded,
d) adverse events are documented, and
e) patients are adequately followed-up.

Overview

This randomized, placebo-controlled clinical trial is expected to demonstrate the efficacy and tolerability of FORMULA A in diarrhea-predominant humans with IBS. Subjects assigned to consume FORMULA A but not a placebo, within 1 hour prior to consuming either meal 1 or meal 2, as well as within 1 hour prior to consuming meal 3 for 4 weeks:

1. Eliminate stool containing a greater ratio of microbiota species from the Bacteroidetes phylum to Firmicutes phylum, and
2. Report adequate relief for all 4 weeks, and
3. Report decreased urgency, and
4. Report decreased stool frequency, and
5. Have firm stools within 1 week of starting treatment, General In this study, subjects are randomly selected to consume 180 ml of either FORMULA A formula or placebo formula orally within 1 hour prior to ingestion of either meals 1 or 2 as well as within 1 hour prior to consumption of meal 3 each day. The subjects and experimenters are blinded to the treatment assignments. Placebo formula contains cellulose with food coloring and flavor to match the total dietary fiber content (8.75 g) of FORMULA A. Placebo is prepared by Merlin Development at the same time they prepare FORMULA A. Both formulations are coded by Merlin Development and the code is maintained with them as well as is held in confidence by a pharmacist at the study clinic until all data are collected at the end of study.

Subjects report weekly for measurements and assessment of any side effects. They are asked to collect a stool sample before initiating FORMULA A or Placebo intervention as well as at the end of the 4 week treatment period. During the screening, treatment, and follow-up periods, daily and weekly symptom data are collected using an interactive telephone-based system.

Pain and bowel function data are collected during the screening phase to ensure that patients had a suitable symptom level at study entry. Severity of pain and discomfort was assessed daily on a 5-point scale (0, none; 1, mild; 2, moderate; 3, intense; and 4, severe). Stool consistency data are monitored daily and scored as follows: 1, very hard: 2, hard; 3, formed; 4, loose; and 5, watery. Absence of stool was assigned a value of 0. Patients also record their IBS symptoms urgency (0%, feel no need to evacuate—100%, feel severe need to evacuate), stool frequency (# of stools per day), bloating (0, no sensation of extended abdomen; 1, mild; 2, moderate; 3, severe) and sense of incomplete evacuation (0, sensation of complete evacuation; 1, incomplete; 2, constipated) daily during the treatment and follow-up phases.

Subject Screening and Selection

Patients with IBS and a diarrhea-predominant bowel pattern aged 18 years or older are enrolled in this study if their symptoms fulfilled the Rome I criteria for IBS for at least 6 months. Patients undergo a 2-week screening evaluation to confirm sufficient level of pain and stool consistency before randomization. Since no objective criteria exist for subgrouping of IBS patients, physicians are asked to assess patients according to predominant pattern of bowel function based on the patient's disease history. Physicians are provided with a guideline based on the percentage of time the patient had experienced diarrhea. If diarrhea is present for 75% of the time, then the patient is classified as being diarrhea predominant.

Patients are excluded if they are pregnant, breastfeeding, or not using approved methods of contraception (if of child-bearing potential); if an unstable medical or other gastrointestinal condition exists; if there is a major psychiatric disorder or substance abuse within the previous 2 years; if an investigational drug was used within 30 days of the screening phase; or if a prohibited concurrent medication (likely to interfere with gastrointestinal tract function or analgesia) was used within 7 days before entering the screening phase.

Pain and bowel function data are collected during the screening phase to ensure that patients had a suitable symptom level at study entry as described above.

Appropriate Symptom and Laboratory Evaluation Evaluations are performed at the screening of potential participants, at the beginning of the study, daily, and at the end of the 4 week treatment period.

1) Beginning of Study and Daily:
  a) Severity of pain and discomfort is assessed on a 5-point scale (0, none; 1, mild; 2, moderate; 3, intense; and 4, severe).
  b) Stool consistency data are scored as follows: 1, very hard; 2, hard; 3, formed; 4, loose; and 5, watery. Absence of stool was assigned a value of 0.
  c) Urgency (0%, feel no need to evacuate—100%, feel severe need to evacuate),
  d) Stool frequency (# of stools per day)
  e) Bloating (0, no sensation of extended abdomen; 1, mild; 2, moderate; 3, severe)
  f) Sense of incomplete evacuation (0, sensation of complete evacuation; 1, incomplete; 2, constipated)
  g) Body weight.
2) Beginning of Study:
Stool is collected and stored frozen but not analyzed until the end of study.
3) End of Study Assessment:
Analysis of the fecal microbiome DNA from both the initial sample and the final sample.

Study Design

Subjects selected for participation are allowed an ad libitum diet. Foods excluded include alcohol. The subjects are encouraged to consume either FORMULA A or Placebo within 1 hour prior to 2 meals each day with ingestion of the test agent being mandatory prior to the $3^{rd}$ meal.

Subjects are given a 4 week supply of ether FORMULA A or Placebo at the onset and are instructed to consume the entire 180 ml volume containing either formula within 1 hour prior to either meals 1 and 2, as well as another 180 ml volume containing either formula within 1 hour prior to meal 3.

Subjects report weekly for measurements and assessment of IBS symptoms. During the screening and treatment periods, daily symptom data are collected using an interactive telephone-based system.

Outcome

This study is expected to demonstrate that FORMULA A and not Placebo:
  1) Increases the ratio of Bacteroidetes species to Firmicutes species in fecal samples when samples at the end of study are compared to samples at the onset of study;
  2) Improves severity of pain and discomfort;
  3) Increases stool consistency;
  4) Decreases urgency to evacuate,
  5) Decreases stool frequency;
  6) Decreases bloating
  7) Increases sense of complete evacuation.

Utilization of FORMULA A to treat idiopathic diarrhea such as a parasitic infection, a viral infection and a symptomatic response to a food is expected to also improve the severity of pain and discomfort, increase stool consistency, decrease the urgency to evacuate, decrease stool frequency, and decrease the sensation of bloating.

Example 7

Case Report of FORMULA A Use in Fecal Bacteriotherapy

A 55 year old woman with chronic diarrhea that was associated with *C. difficile* infection initially presents to her primary care physician diarrhea of 8 months duration that originally started shortly following treatment with cephalosporin and quinolone antibiotics for back surgery and a pulmonary infection. During these eight months, she is repeatedly treated with metronidazole and vancomycin, and required several hospitalizations for intravenous hydration. The patient complains of loose small bowel movements every 15 minutes, accompanied by great urgency and rectal tenesmus. She wears diapers at all times and loses 10% of her body weight. Flexible sigmoidoscopy demonstrates classic pseudomembranous colitis. Stool samples are positive for *C. difficile* toxins A and B, and stool culture confirms heavy growth of this bacterium. The patient is again treated with vancomycin, but fails to respond. She is subsequently prescribed nitazoxanide (2-acetyloxy-N-(5-nitro-2-thiazolyl)benzamide), 500 mg orally, twice daily. Ten days after discontinuation of Nitazoxanide, the patient has recurrence of her original diarrheal symptoms. Endoscopic analysis indicates return of pseudomembranous colitis, and stool studies are again positive for *C. difficile*. Despite two more cycles of Nitazoxanide, including one lasting a full month, and continuous administration of Florastor, a probiotic containing *Saccharomyces boulardii*, the *C. difficile*-induced colitis reoccurrs.

Since conventional treatment fails to resolve the *C. diff*, fecal bacteriotherapy is offered to break the cycle of recurrences and achieve a potential cure. Informed consent is obtained from both the patient and the donor following discussion with each of the potential risks, benefits, and alternative options. The patient is maintained on Nitazoxanide until the day before the procedure. The patient's husband of 44 years (donor) is prescribed FORMULA A 3 times a day for 2 weeks. Fecal donor material is taken from him, who has no risk factors for blood-borne communicable diseases, has no recent exposure to antibiotics, has no gastrointestinal symptoms of any kind, and tests negative for common stool pathogens and *C. difficile*. Bacteriotherapy is delivered into the patient's right colon by way of a colonoscopy. The patient is expected to have her first solid bowel movement on the second day following treatment. It is expected that her abdominal pain gradually subsides, and at one month following bacteriotherapy and it is expected that her stool samples will be negative for *C. difficile*. The patient is expected to commence FORMULA A twice a day. At six months follow-up, the patient is expected to report once-daily formed stools.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A human gastrointestinal microbiome modulating composition for improving blood glucose in a human need thereof, said composition consisting essentially of a therapeutically effective amount of:
i. isolated inulin;
ii. purified dietary β-glucan; and
iii. a berry pomace or a berry pomace extract.

2. The composition according to claim 1, wherein the isolated inulin is present in an amount of at least about 3 g by weight, and wherein the purified dietary β-glucan is present in an amount of at least about 2 g by weight.

3. The composition according to claim 1, wherein the purified dietary β-glucan is purified from a source selected from the group consisting of: baker's yeast, oat, barley, wheat, fungi, mushrooms, bacteria, and combinations thereof.

4. The composition according to claim 1, wherein the purified dietary β-glucan is β-glucan purified from oat.

5. The composition according to claim 1, wherein the gastrointestinal microbiome modulating composition consists essentially of:
i. at least about 3 g of isolated inulin;
ii. at least about 2 g of a purified dietary β-glucan; and
iii. at least about 700 mg of berry pomace or berry pomace extract.

6. The composition according to claim 5, wherein the blueberry pomace or berry pomace extract is present in an amount of about 4.7 g.

7. The composition according to claim 1, wherein the purified dietary β-glucan is purified from wheat.

8. The composition according to claim 1, wherein the purified dietary β-glucan is purified from barley.

9. The composition according to claim 1, wherein the isolated inulin is agave inulin.

10. The composition according to claim 5, wherein:
i. the isolated inulin is present in an amount of 4-40% by weight;
ii. the purified dietary β-glucan is present in an amount of 2-21% by weight; and
iii. the berry pomace or berry pomace extract is present in an amount of 0.5-9% by weight.

11. The composition according to claim 5, wherein:
i. the isolated inulin is present in an amount of 6.5-28% by weight;
ii. the purified dietary β-glucan is present in an amount of 3.5-14% by weight; and
iii. the berry pomace or berry pomace extract is present in an amount of 1-6% by weight.

12. A tablet or capsule consisting essentially of a) isolated inulin, b) purified β-glucan, and c) a berry pomace or a berry pomace extract.

13. The tablet or capsule according to claim 12, wherein the isolated inulin is at least about 3 g of isolated inulin, and wherein the dietary β-glucan extract is at least about 2 g of dietary β-glucan extract.

14. The tablet or capsule according to claim 12, wherein the purified dietary β-glucan is purified from a source selected from the group consisting of: baker's yeast, oat, barley, wheat, fungi, mushrooms, bacteria, and combinations thereof.

15. The tablet or capsule according to claim 12, wherein the purified dietary β-glucan is β-glucan purified from oat.

16. The tablet or capsule according to claim 12, wherein the gastrointestinal microbiome modulating composition consists essentially of:
i. at least about 3 g of isolated inulin;
ii. at least about 2 g of a purified dietary β-glucan extract; and
iii. at least about 700 mg of berry pomace or berry pomace extract.

17. The tablet or capsule according to claim 16, wherein the berry pomace or berry pomace extract is present in an amount of about 4.7 g.

18. The tablet or capsule according to claim 12, wherein the purified dietary β-glucan is purified from wheat.

19. The tablet or capsule according to claim 12, wherein the purified β-glucan is purified from barley.

20. The tablet or capsule according to claim 12, wherein the isolated inulin is agave inulin.

21. The tablet or capsule according to claim 16, wherein:
i. the isolated inulin is present in an amount of 4-40% by weight;
ii. the purified dietary β-glucan is present in an amount of 2-21% by weight; and
iii. the berry pomace or berry pomace extract is present in an amount of 0.5-9% by weight.

22. The tablet or capsule according to claim 16, wherein:
i. the isolated inulin is present in an amount of 6.5-28% by weight;
ii. the purified dietary β-glucan is present in an amount of 3.5-14% by weight; and
iii. the berry pomace or berry pomace extract is present in an amount of 1-6% by weight.

* * * * *